(12) United States Patent
Jacofsky et al.

(10) Patent No.: US 8,926,669 B2
(45) Date of Patent: Jan. 6, 2015

(54) MODULAR POLYAXIAL PEDICLE SCREW SYSTEM

(75) Inventors: Marc C. Jacofsky, Phoenix, AZ (US); A. Joshua Appel, Paradise Valley, AZ (US)

(73) Assignee: The Center for Orthopedic Research and Education, Inc., Phoenix, AZ (US)

( * ) Notice: Subject to any disclaimer, the term of this patent is extended or adjusted under 35 U.S.C. 154(b) by 1248 days.

(21) Appl. No.: 12/080,107

(22) Filed: Mar. 28, 2008

(65) Prior Publication Data

US 2008/0262556 A1 Oct. 23, 2008

Related U.S. Application Data

(63) Continuation-in-part of application No. 11/890,058, filed on Aug. 3, 2007, now Pat. No. 8,167,912.

(60) Provisional application No. 60/903,957, filed on Feb. 27, 2007.

(51) Int. Cl.
*A61B 17/70* (2006.01)
*A61B 17/86* (2006.01)

(52) U.S. Cl.
CPC .......... *A61B 17/7032* (2013.01); *A61B 17/7037* (2013.01); *A61B 17/7076* (2013.01); *A61B 17/8605* (2013.01)
USPC ........... 606/264; 606/265; 606/300; 606/305; 606/308

(58) Field of Classification Search
CPC ........... A61B 17/7032; A61B 17/7034; A61B 17/7035
USPC ................. 606/246–279, 300–321
See application file for complete search history.

(56) References Cited

U.S. PATENT DOCUMENTS

| | | |
|---|---|---|
| 4,573,454 A | 3/1986 | Hoffman |
| 4,946,458 A | 8/1990 | Harms et al. |

(Continued)

OTHER PUBLICATIONS www.blackstonemedical.com "Thoracolumbar Systems" web page, 2005, Blackstone Medical, Inc.

(Continued)

*Primary Examiner* — Mary Hoffman
*Assistant Examiner* — Christina Negrellirodrigue
(74) *Attorney, Agent, or Firm* — Ballard Spahr LLP

(57) ABSTRACT

There is provided a modular polyaxial pedicle screw assembly that includes various components which may be configured in various manners so as to provide different functionalities to the pedicle screw assembly. This advantageously decreases surgery time, reduces repetitive and tedious surgical steps, and allows for streamlining inventory of expensive medical equipment. In one embodiment, a pedicle screw assembly includes a pedicle screw, a rod holding element, a polyaxial insert, a rod, and a set screw. The pedicle screw includes a threaded shaft and a cap. The rod holding element includes a screw hole, an insert bearing area, a chamber, chamber walls, a saddle area, and a threading area. The insert is disposed within the chamber, and the insert defines a bearing surface, an upper surface, side walls and a receiving area. The insert is positioned within the chamber such that the insert bearing surface contacts the rod holding element insert bearing area; additionally the side walls of the insert can bear against the chamber walls. The pedicle screw is positioned so that the screw shaft passes through the screw hole of the rod holding element and the screw cap rests within the receiving area of the insert. The rod is disposed so as to rest on the upper surface of the insert; and the set screw, joined to the threading area of the rod holding element, secures the rod to the upper surface of the insert.

20 Claims, 19 Drawing Sheets

(56) References Cited

U.S. PATENT DOCUMENTS

| | | |
|---|---|---|
| 5,176,678 A | 1/1993 | Tsou |
| 5,360,431 A | 11/1994 | Puno et al. |
| 5,474,555 A | 12/1995 | Puno et al. |
| 5,690,630 A | 11/1997 | Errico et al. |
| 5,725,528 A | 3/1998 | Errico et al. |
| 5,873,878 A * | 2/1999 | Harms et al. ............... 606/308 |
| 5,879,350 A | 3/1999 | Sherman et al. |
| 6,010,503 A | 1/2000 | Richelsoph et al. |
| 6,053,917 A | 4/2000 | Sherman et al. |
| 6,077,262 A * | 6/2000 | Schlapfer et al. ............. 606/305 |
| 6,113,601 A | 9/2000 | Tatar |
| 6,287,311 B1 | 9/2001 | Sherman et al. |
| 6,402,752 B2 | 6/2002 | Schaffler-Wachter et al. |
| 6,488,681 B2 | 12/2002 | Martin et al. |
| 6,565,567 B1 | 5/2003 | Haider |
| 6,660,004 B2 | 12/2003 | Barker et al. |
| 6,716,214 B1 | 4/2004 | Jackson |
| 6,840,940 B2 | 1/2005 | Ralph et al. |
| 6,869,433 B2 | 3/2005 | Glascott |
| RE39,035 E | 3/2006 | Finn et al. |
| 7,018,378 B2 | 3/2006 | Biedermann et al. |
| RE39,089 E | 5/2006 | Ralph et al. |
| 7,087,057 B2 | 8/2006 | Konieczynski et al. |
| RE39,325 E | 10/2006 | Bryan |
| 7,118,571 B2 | 10/2006 | Kumar et al. |
| 7,819,901 B2 * | 10/2010 | Yuan et al. .................... 606/264 |
| 2004/0249380 A1 | 12/2004 | Glascott |
| 2004/0260284 A1 | 12/2004 | Parker |
| 2005/0216003 A1* | 9/2005 | Biedermann et al. ........... 606/61 |
| 2005/0261687 A1* | 11/2005 | Garamszegi et al. ........... 606/61 |
| 2006/0084981 A1 | 4/2006 | Shluzas |
| 2006/0106380 A1* | 5/2006 | Colleran et al. ................ 606/61 |
| 2006/0149235 A1 | 7/2006 | Jackson |
| 2006/0212034 A1 | 9/2006 | Triplett et al. |
| 2006/0229607 A1 | 10/2006 | Brumfield |
| 2006/0235385 A1 | 10/2006 | Whipple |
| 2006/0241593 A1 | 10/2006 | Sherman et al. |
| 2006/0241594 A1 | 10/2006 | McCarthy et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0247631 A1 | 11/2006 | Ahn et al. |
| 2006/0271047 A1 | 11/2006 | Jackson |
| 2006/0271048 A1 | 11/2006 | Thramann |
| 2006/0276789 A1 | 12/2006 | Jackson |
| 2006/0276792 A1 | 12/2006 | Ensign et al. |
| 2006/0293665 A1 | 12/2006 | Shluzas |
| 2006/0293666 A1 | 12/2006 | Matthis et al. |
| 2007/0270808 A1* | 11/2007 | Drewry et al. .................. 606/61 |
| 2008/0086132 A1 | 4/2008 | Biedermann et al. |
| 2008/0119858 A1 | 5/2008 | Potash |
| 2008/0195150 A1 | 8/2008 | Bishop |
| 2008/0234757 A1 | 9/2008 | Jacofsky |

OTHER PUBLICATIONS www.blackstonemedical.com/icon.php "Icon Modular Spinal Fixation System" web page, 2007, Blackstone Medical, Inc.

Non Final Office Action issued Jan. 11, 2011 re U.S. Appl. No. 11/890,058, filed Aug. 3, 2007.

Petition to Withdraw Holding of Abandonment filed 6/23/10 re U.S. Appl. No. 11/890,058, filed Aug. 3, 2007.

Notice of Abandonment issued Jun. 11, 2010 re U.S. Appl. No. 11/890,058, filed Aug. 3, 2007.

Response to Restriction Requirement filed Dec. 21, 2009 re U.S. Appl. No. 11/890,058, filed Aug. 3, 2007.

Election/Restriction Requirement issued Nov. 24, 2009 re U.S. Appl. No. 11/890,058, filed Aug. 3, 2007.

Response to Non Final Office Action filed Apr. 11, 2011 re U.S. Appl. No. 11/890,058, filed Aug. 3, 2007.

Non Final Office Action dated Jun. 28, 2011 re U.S. Appl. No. 11/890,058.

* cited by examiner

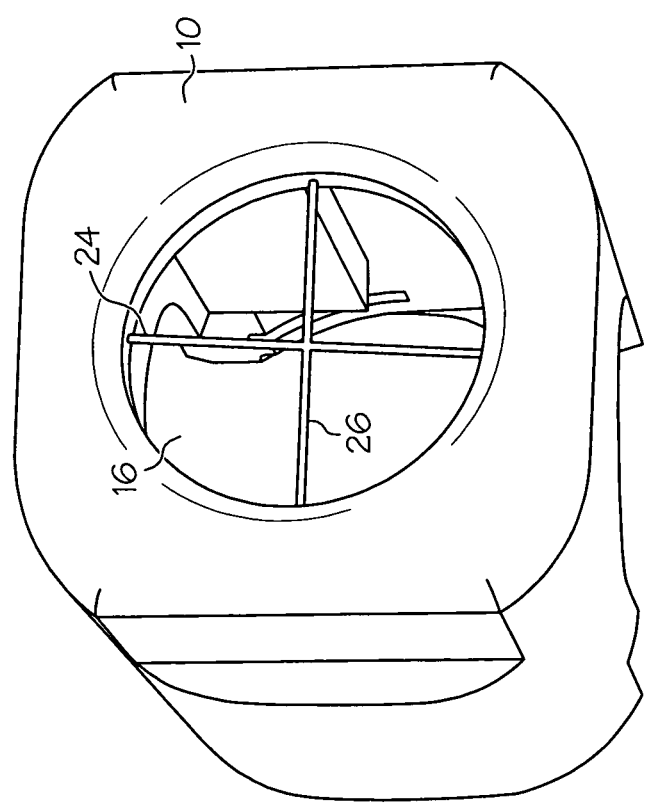

MODULAR POLYAXIAL PEDICLE SCREW SYSTEM

CROSS REFERENCE TO RELATED APPLICATIONS

This application is a continuation-in-part application claiming priority from the utility patent application Ser. No. 11/890,058 filed Aug. 3, 2007 now U.S. Pat. No. 8,167,912 which claims priority from the provisional patent application Ser. No. 60/903,957 filed Feb. 27, 2007, both in the name of Marc C. Jacofsky and A. Joshua Appel entitled "Modular Pedicle Screw System" and incorporated herein by reference.

FIELD OF THE INVENTION

The present invention relates to medical devices. More particularly, the invention relates to pedicle screw systems and methods for use in spinal fixation surgeries and therapies.

BACKGROUND OF THE INVENTION

Spinal surgery procedures often require securing various implants to vertebrae of the spine. One such implant is the pedicle screw and its related components. Other components, such as rods, are then secured to individual pedicle screw implants in order to provide a support or fixation function between and among neighboring vertebrae. Both the rods and screws may have varying diameters and dimensions depending on patient and therapeutic needs. Due to the complex curvature and anatomy of the spine it is difficult to align the bone screw and rod holder assembly with the rod, particularly when spanning multiple segments. Traditionally, this required extensive bending and test fitting of rods to correctly approximate the rod holding portion of the pedicle screw. More recently, the polyaxial screw type has become widely available, which allows the rod receiving portion of the screw to pivot about the screw head. The pivoting head allows the rod holder to interface with the rod with only minimal rod contouring. These polyaxial screws are now the most common type of pedicle screw used today.

Current pedicle screw designs consist of several component parts including: 1) a threaded bone screw shaft which is anchored into the pedicle bone of the vertebrae 2) a rod holding member which is attached to the head of the bone screw to receive a rod for stabilization of the spine, and 3) a set screw which interfaces with the top of the rod holder to secure the rod into the holder to form a stable construct. These components are assembled into two primary design types: monoaxial and polyaxial screw systems. The monoaxial screws typically have a fixed angular relationship between the bone screw and rod holder. These screw designs dictate that the rod is held perpendicular to the direction of the bone screw. While these designs are strong and stable, they make it difficult to position the screw and rod properly and require a lot of rod bending to correctly approximate the rod holder and rod. Polyaxial designs allow the rod holding member to pivot on the bone screw head such that the rod holder can properly interface with a rod that is not perfectly perpendicular to the direction that the bone screw is inserted. After the set screw is used to secure the rod into the rod holder, the polyaxial design will lock into place and no longer allow the rod holder to pivot on the screw head.

Current designs suffer from some limitation in their functionality and the manufacturing requirements to encompass the myriad variations of particular surgical approaches. For example, many companies must offer both a monoaxial and polyaxial screw set, each with applications for specific surgical procedures. Similarly, current designs rely on rod holders that are designed for one specific rod diameter. Thus, if a manufacturer wants to offer a system that can use both 5.5 mm and 6.0 mm rods, they must manufacture two different sized rod holders, and they must manufacture both monoaxial and polyaxial variants of each size holder. This necessitates holding an inventory of parts in surgical centers, hospitals, and supply houses, many of which are rarely used.

Another limitation of current pedicle screw systems is a tendency for the set screw threads to cross-thread when approximated with the rod holding element. This may complicate assembly during operative procedures and increase procedure time to the detriment of the patient. Additionally, set screws that are cross-threaded or over-torqued can cause head splay, whereby the top portion of the rod holding element is deformed outward by the set screw. This causes poor rod stability and often necessitates the removal and replacement of the pedicle screw, again, increasing operative time, damage to the pedicle bone and the potential for surgical complications. Undetected head splay at the time of surgery could also lead to premature failure of the construct and necessitate additional surgical procedures at a later time. It is therefore advantageous to eliminate cross threading of the set screw and prevent head splay of the rod holding element to any extent possible.

An additional shortcoming in current systems is the inability to create a uniplanar pedicle screw configuration that is able to pivot in only one plane of motion rather than the combined motions of the polyaxial design. A uniplanar design is useful in complex spinal reconstructive cases where multiple segments are spanned with stabilizing rods and when lateral forces must be applied to a vertebrae to bring it into alignment with neighboring segments. With the traditional polyaxial designs, a lateral force applied to the rod holding element will cause the rod holder to pivot on the bone screw head rather than rotate the vertebral body into a desired alignment.

Hence there has been identified a need to provide an improved pedicle screw device as well as systems and methods of employing and utilizing pedicle screw assemblies. For example, it is desired that an improved pedicle screw assembly allow for a reduction of the necessary inventory of expensive medical components. The present invention addresses one or more of these long felt but unmet needs.

SUMMARY OF THE INVENTION

The system proposed herein allows for a multipurpose pedicle screw assembly having multiple modular inserts. The combination of modular inserts allows the screw assembly to perform with different functionalities that would be applicable with different surgical procedures. The selection of a particular kind of modular insert can determine the assembly functionality. The modular pedicle screw assembly may additionally incorporate a rod adapter that allows multiple sized rods to be used with the same rod holding element. The differing screw configurations allow for a variety of screw functions that can all be achieved while using the same basic rod holding element, which is often the most machining intensive component of any pedicle screw.

In one embodiment, and by way of example only, there is provided a polyaxial pedicle screw assembly that includes a polyaxial pedicle screw, a rod holding element, a polyaxial insert, a rod, and a set screw. The polyaxial pedicle screw has a shaft and head. The rod holding element defines a screw hole, an insert bearing area, a chamber, a saddle area, a cutaway area, a head seating surface, and a threading area. The polyaxial insert is disposed within the chamber of the rod holding element, and the insert defines a bearing surface, a screw head bearing surface, and an upper surface; further the polyaxial insert is positioned within the chamber of the rod holding element such that the insert bearing surface of the rod holding element contacts the rod holding element insert bearing area. The pedicle screw is disposed so that the shaft passes through the screw hole, and the pedicle screw head contacts the screw head bearing surface of the polyaxial insert. The rod is disposed to rest on the upper surface of the polyaxial insert; and the set screw is joined to the threading area of the rod holding element so as to secure the rod to the upper surface of the insert and to lock the polyaxial screw and rod holding element into a desired position. The rod holding element may further define a notch, and the polyaxial insert may further comprise guide pins positioned such that the guide pins fit within the notch when the polyaxial insert is disposed in the chamber. The guide pins may be substantially cylindrical in shape, such that the polyaxial insert has freedom of movement in a plane by rotating around the guide pins. The rod holding element may also include a head seating surface disposed proximate to the screw hole, and wherein the pedicle screw head contacts the head seating surface. The insert bearing area of the rod holding element and the bearing surface of the polyaxial insert may have substantially the same circular shape. The polyaxial screw head may include surface structures such as ridges.

In a further embodiment, also by way of example only, there is provided a medical kit that includes as components of the kit: a polyaxial screw, a rod holding element, a polyaxial insert, and a set screw. The medical kit may also include additional elements such as a rod, a uniplanar insert, a monoaxial insert, a rod adapter, and at least two rods having different diameters.

In still a further embodiment, and still by way of example only, there is provided a method for forming a polyaxial screw assembly comprising the steps of: positioning a polyaxial screw with a shaft relative to a rod holding element having a screw hole such that the shaft of the polyaxial screw passes through the screw hole of the rod holding element; positioning a polyaxial insert such that a screw head bearing surface of the polyaxial insert contacts the head of the polyaxial screw; positioning a rod within the rod holding element; and joining a set screw to the rod holding element. The step of positioning a polyaxial insert mentioned above may further include positioning the polyaxial insert such that guide pins of the polyaxial insert fit within notches of the rod holding element. The method may also include the step of rotating the insert relative to the rod holding element by rotating the polyaxial insert around the axis passing through the guide pins. And the method may also include the step of adjusting the position of the polyaxial screw relative to the rod holding element by moving the screw head at the screw head bearing surface of the polyaxial insert. A further step of positioning a rod adapter around the rod may also be included in the method. Finally, the method may further include the step of fixing the polyaxial screw, the polyaxial insert, and the rod holding element into a desired substantially immovable configuration by way of the set screw.

Other independent features and advantages of the polyaxial pedicle screw assembly will become apparent from the following detailed description, taken in conjunction with the accompanying drawings which illustrate, by way of example, the principles of the invention.

BRIEF DESCRIPTION OF THE DRAWINGS

FIG. 20 is a bottom perspective view of a rod holding element, according to an embodiment of the present invention;

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background of the invention or the following detailed description of the invention. Reference will now be made in detail to exemplary embodiments of the invention, examples of which are illustrated in the accompanying drawings. Wherever possible, the same reference numbers will be used throughout the drawings to refer to the same or like parts.

Uniplanar and Monoaxial Embodiments

Figure 1:
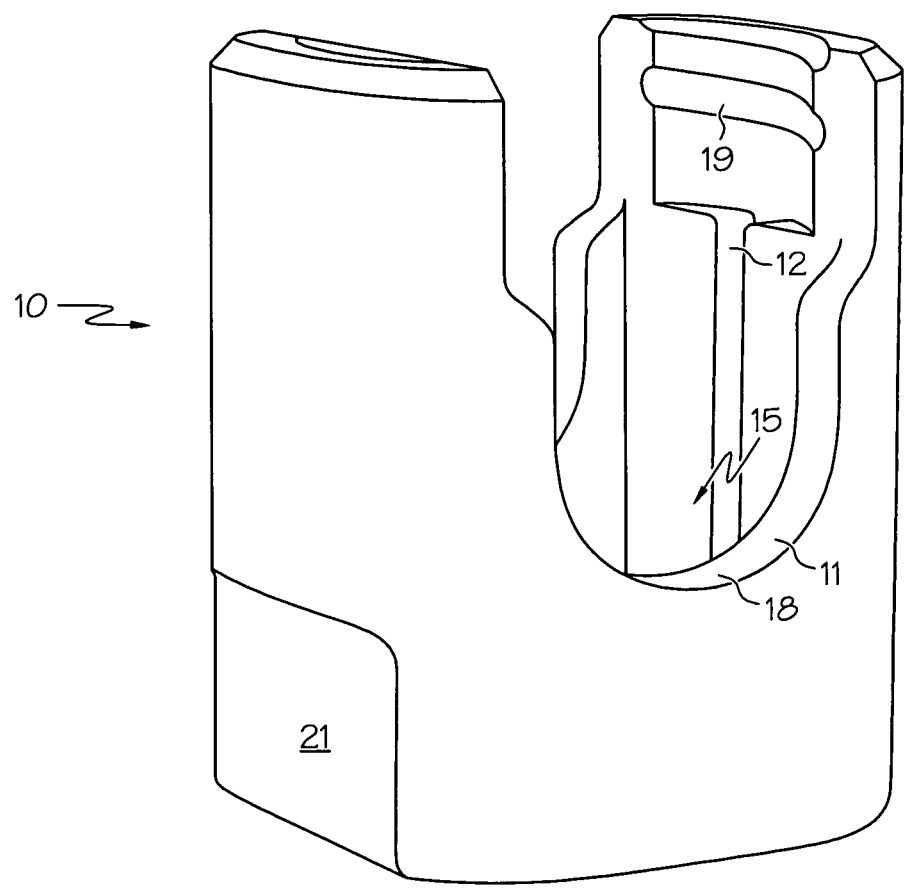
FIG. 1 is a perspective view of a rod holding element, according to an embodiment of the present invention.
Figure 2:
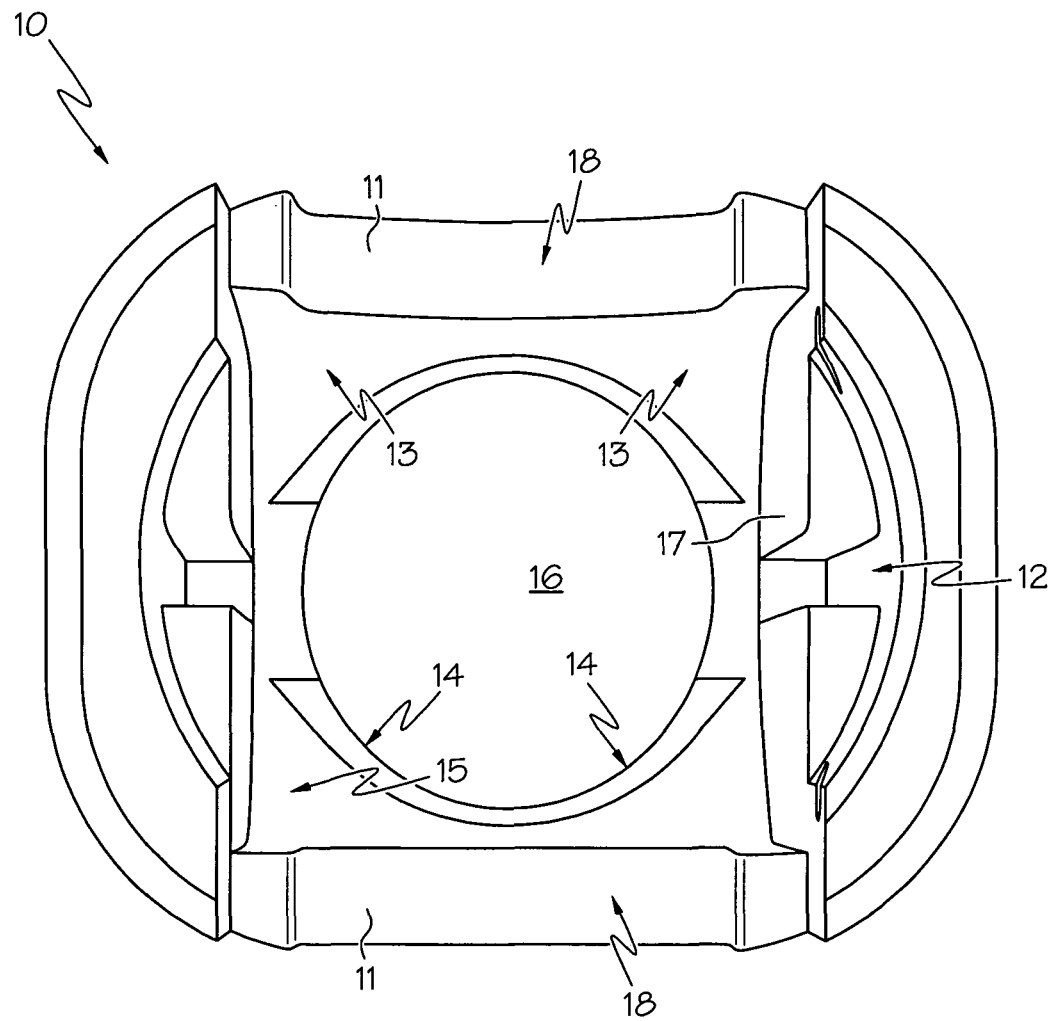
FIG. 2 is a top view of a rod holding element, according to an embodiment of the present invention.
Figure 3:
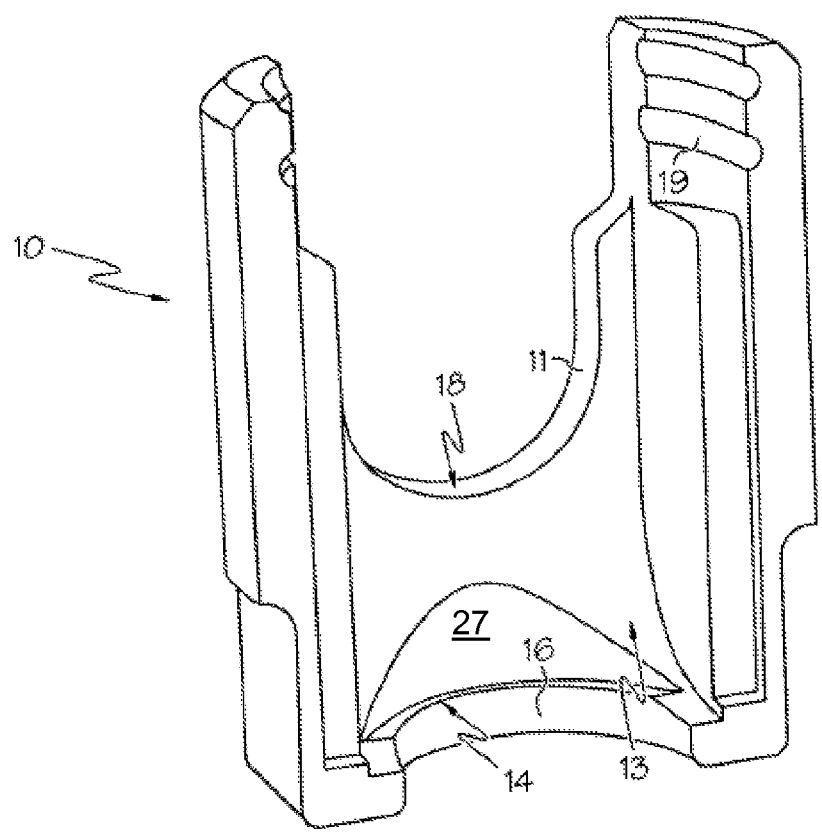
FIG. 3 is a partial cutaway view of a rod holding element, according to an embodiment of the present invention.

Referring initially to FIGS. 1, 2, and 3 there is illustrated a first embodiment of rod holding element 10. As further explained herein, rod holding element 10 functions as a structure with which various components cooperate in order to create a pedicle screw assembly. Thus, in one embodiment, rod holding element 10 includes various features which are designed to cooperate with other pieces, and these features of rod holding element 10 include rod cradle 11, insert notch 12, bearing surface 13, and polyaxial head seating surface 14. The rod holding element 10 is versatile in that this single element can be used to assemble different kinds of pedicle screws including static monoaxial screw, uniplanar screw, and polyaxial screw assemblies.

Rod holding element 10 is characterized by an opening 16. Opening 16 is sized such that a tip and shaft of a bone screw (not shown) can pass from an interior chamber area 15 of rod holding element 10 to the exterior of rod holding element 10. Rod holding element 10 further defines chamber walls 17 which also define and limit chamber area 15. An insert, as explained further herein, can be placed within chamber area 15.

Figure 4:
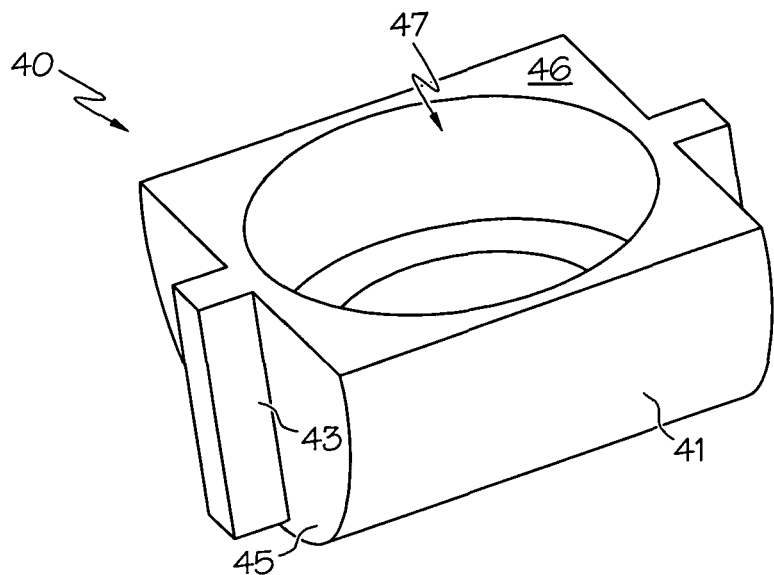
FIG. 4 is a perspective view of a monoaxial insert, according to an embodiment of the present invention.
Figure 5:
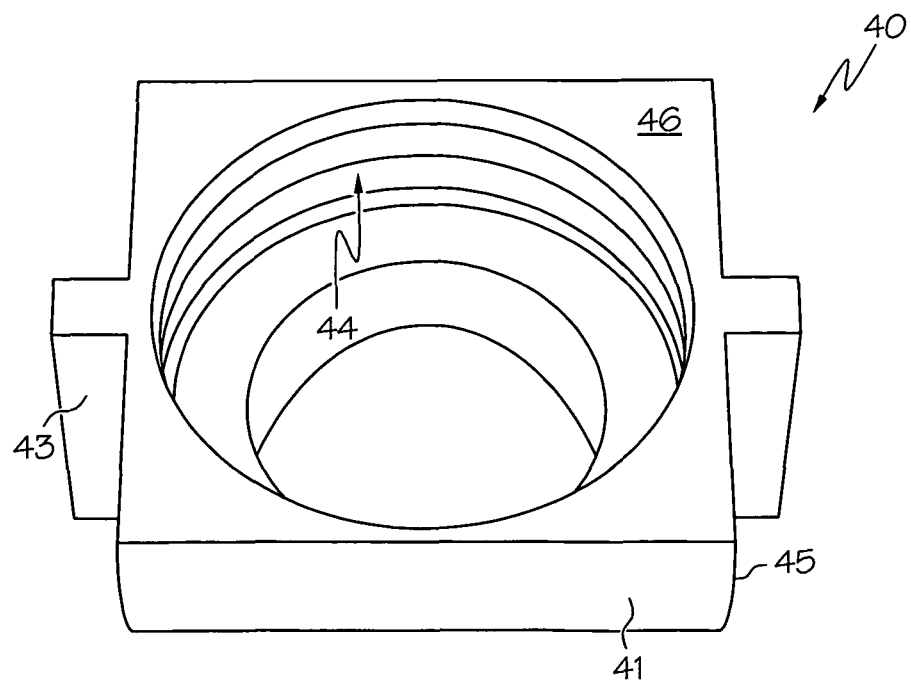
FIG. 5 is a further perspective view of a monoaxial insert, with a threaded area, according to an embodiment of the present invention.
Figure 6:
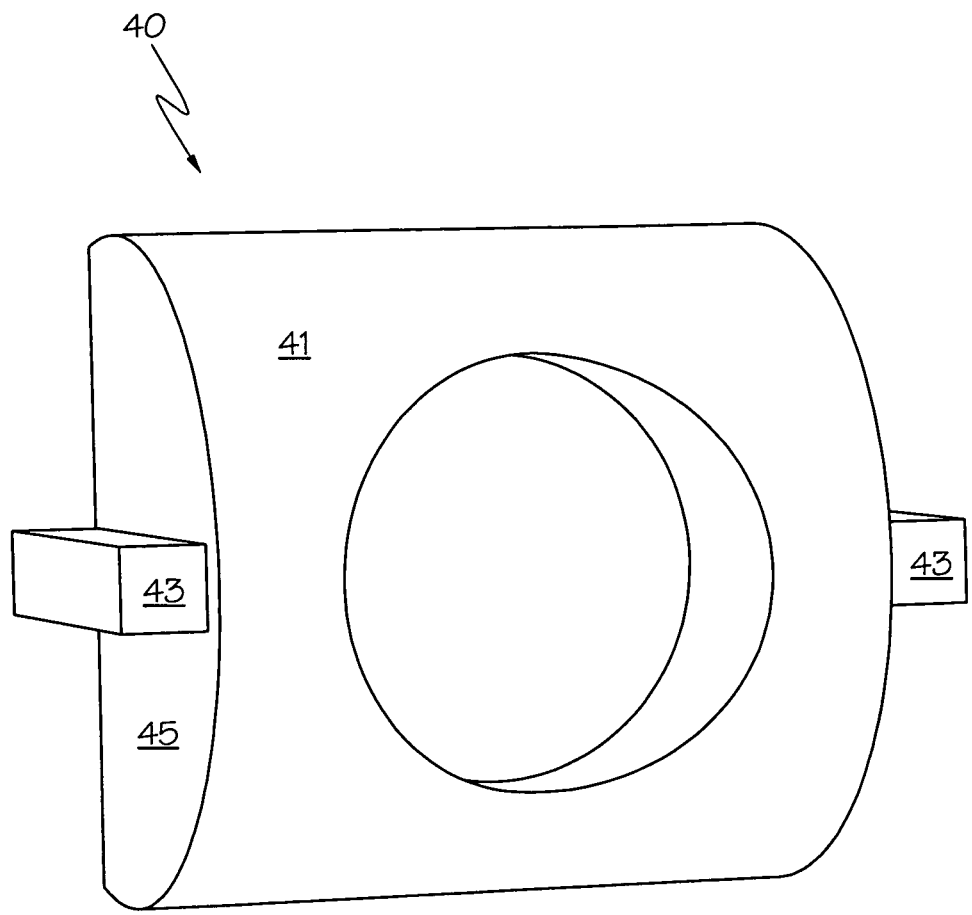
FIG. 6 is a further bottom perspective view of a monoaxial insert, according to an embodiment of the present invention.

Referring next to FIGS. 4, 5, and 6, there is illustrated an embodiment of a monoaxial insert 40. Monoaxial insert 40 includes bearing surface 41, locking tabs 43, and in some embodiments, threading 44. Bearing surface 41 is preferably designed so that bearing surface contacts rod holding element bearing surface 13 when monoaxial insert 40 is fully placed within rod holding element 10. Further, locking tabs 43 are designed so as to fit within the space defined by insert notch 12 of rod holding element 10. Preferably, locking tabs 43 are designed to fit within notch 12 so that when monoaxial insert 40 is fully assembled with rod holding element 10 the contact between locking tabs 43 and notch 12 substantially restricts any movement of monoaxial insert 40. As explained further herein, locking tabs 43 and notch 12 may be configured with a mutually fitting dovetail shape. Thus, in effect, monoaxial insert 40 is held to a single or static position within rod holding element 10.

FIGS. 4 and 5 illustrate embodiments of monoaxial insert 40 that do not include threading and that do include threading 44 respectively. As will be understood by those skilled in the art, threading 44 such as illustrated in FIG. 5 can be used to secure a threaded bone screw head to the insert. However, the threading aspect of monoaxial insert 40 does not affect the above-described position locking of monoaxial insert 40 with respect to rod holding element 10.

Figure 7:
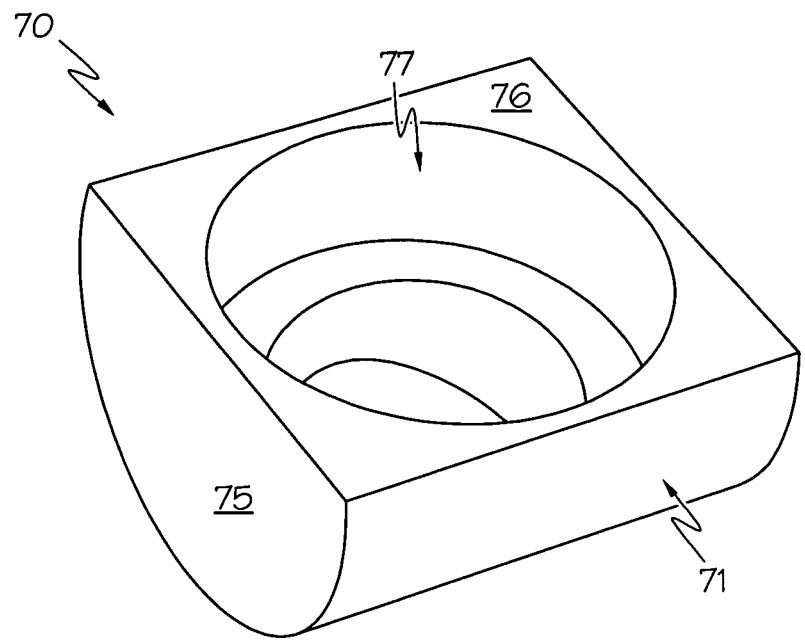
FIG. 7 is a perspective view of a uniplanar insert, according to an embodiment of the present invention.
Figure 8:
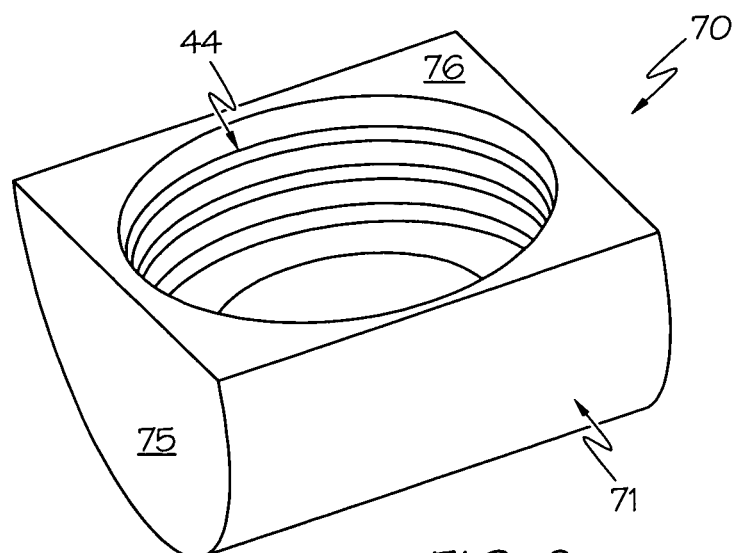
FIG. 8 is a further perspective view of a uniplanar insert, with a threaded area, according to an embodiment of the present invention.
Figure 9:
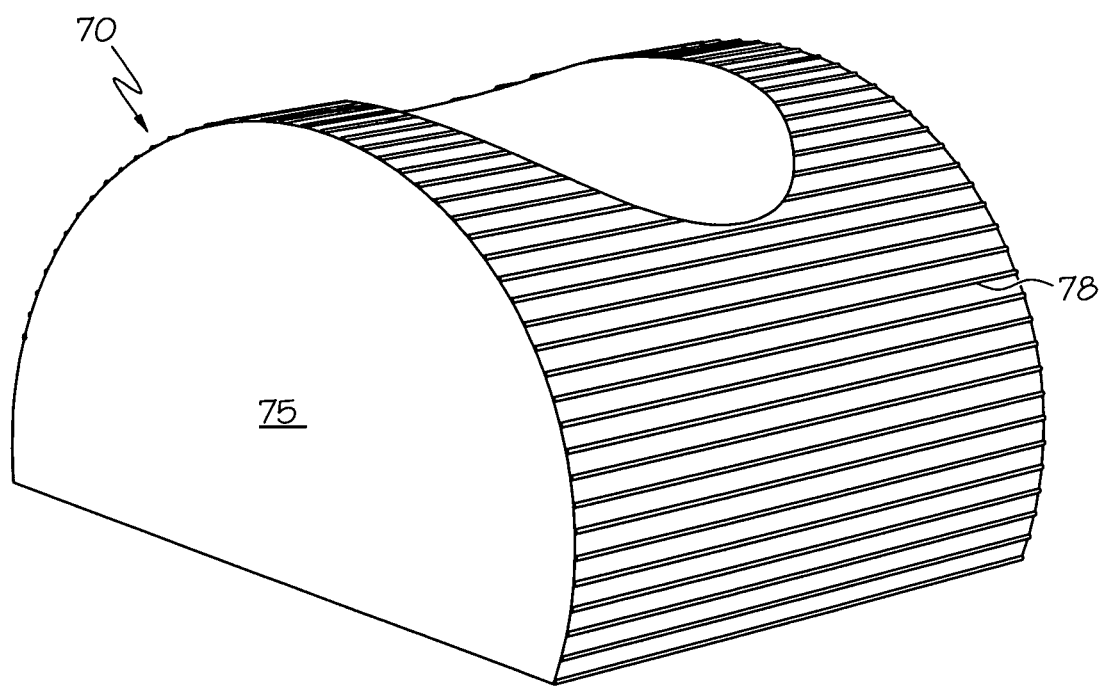
FIG. 9 is a further perspective view of a uniplanar insert, with a corrugated bearing surface, according to an embodiment of the present invention.

Referring now to FIGS. 7, 8, and 9, there is illustrated an embodiment of a uniplanar insert 70. It will be apparent that the overall shape and configuration of uniplanar insert 70 is similar, but not identical, to monoaxial insert 40. For example, both monoaxial insert 40 and uniplanar insert 70 have an external shape that allows them to slide into opening 16 defined by rod holding element 10. However, in a point of difference, uniplanar insert 70 does not include locking tabs 43. Thus, for example, when disposed within opening 16, uniplanar insert 70 is not completely restricted from movement. Rather, when seated so that bearing surface 71 of uniplanar insert contacts bearing surface 41 of rod holding element 10, uniplanar insert 70 has two degrees of freedom so that it can have a movement when these bearing surfaces 71 and 41 move relative to one another. However, uniplanar insert 70 does not have a third degree of freedom in that side walls 75 of uniplanar insert are in substantial contact with chamber wall 17 of rod holding element 10 and so restricted in movement. Thus, with two degrees of freedom, uniplanar insert 70 can move within a plane of motion relative to rod holding element 10.

Both a monoaxial insert 40 and a uniplanar insert 70 may share certain common features. For example both inserts 40 and 70 may include side walls 45 and 75. Further both inserts 40, 70 may also include an upper surface 46 and 76. In a preferred embodiment, side walls 45, 75 and upper surface 46, 76 are substantially planar in configuration. Inserts 40 and 70 may be configured such that when insert is placed within chamber area, side walls 45 and 75 substantially contact chamber walls 17 thereby restricting the movement of insert within rod holding element 10. Additionally, both inserts 40 and 70 may include a hole (not shown) through which a bone screw (not shown) may pass; and they may also include a receiving area 47 and 77 shaped to receive the head of a bone screw as explained further herein. The shape of this receiving surface and congruent surface of the bone screw is not limited in scope by the preferred embodiment. Those skilled in the art will recognize that a conical tapered press fit could also be utilized to mate and secure the insert and bone screw head. Finally, both inserts 40 and 70 may also include threading for joining with a bone screw.

It will here be appreciated that the movement heretofore described for the monoaxial insert 40 and uniplanar insert 70 assumes that both inserts stay in a fully bottomed contact with rod holding element 10. Until final assembly of a pedicle screw assembly, both monoaxial insert 40 and uniplanar insert 70 could be removed from opening 16 of rod holding element, a generally vertical movement (relative to the figures). However, it will be appreciated that the placement of monoaxial insert 40 and uniplanar insert 70 within chamber 16 accomplishes a preassembly which will ultimately lead to a final assembly of a pedicle screw assembly. Thus, the potential movement of removing the inserts 40 and 70 has been ignored.

In a preferred embodiment, the insert 40 and 70 are convex and cylindrical in shape on their bearing surface 41, 71 where the insert contacts the reciprocal bearing surface 13 of the rod holding element 10. Thus the curvature of bearing surface 41, 71 of insert 40, 70 preferably closely matches the curvature of rod holding element bearing surface 13. The matching of these two surfaces forms, in one embodiment, a partial cylindrical bearing on which the insert can glide. If desired, bearing surfaces 41, 71 of inserts 40, 70 can be machined (or otherwise formed) with corrugations or ridges 78 as shown specifically in FIG. 9. Ridge-like structures 78 can aide in locking the assembly into a desired configuration when bearing surfaces are compressed together.

Figure 11:
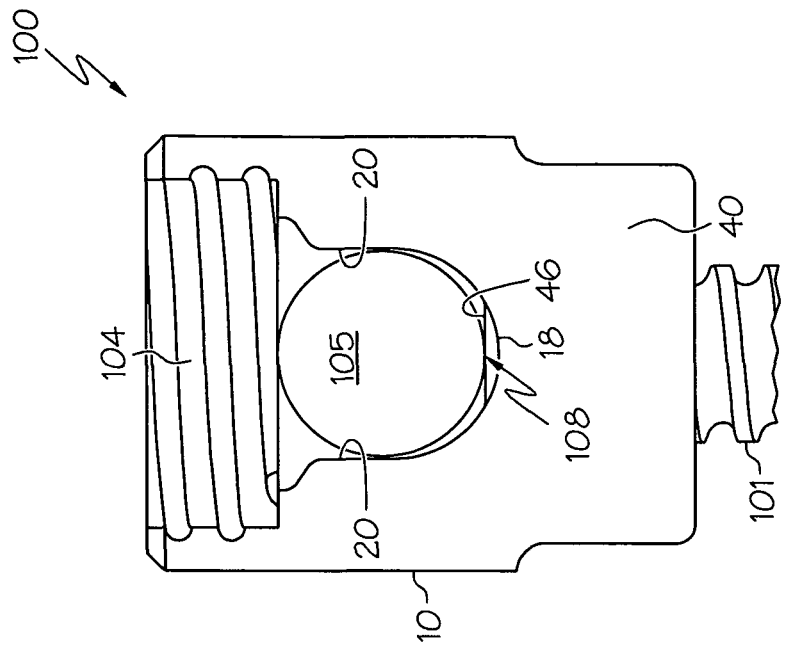
FIG. 11 is a front view of a pedicle screw assembly, according to an embodiment of the present invention.
Figure 10:
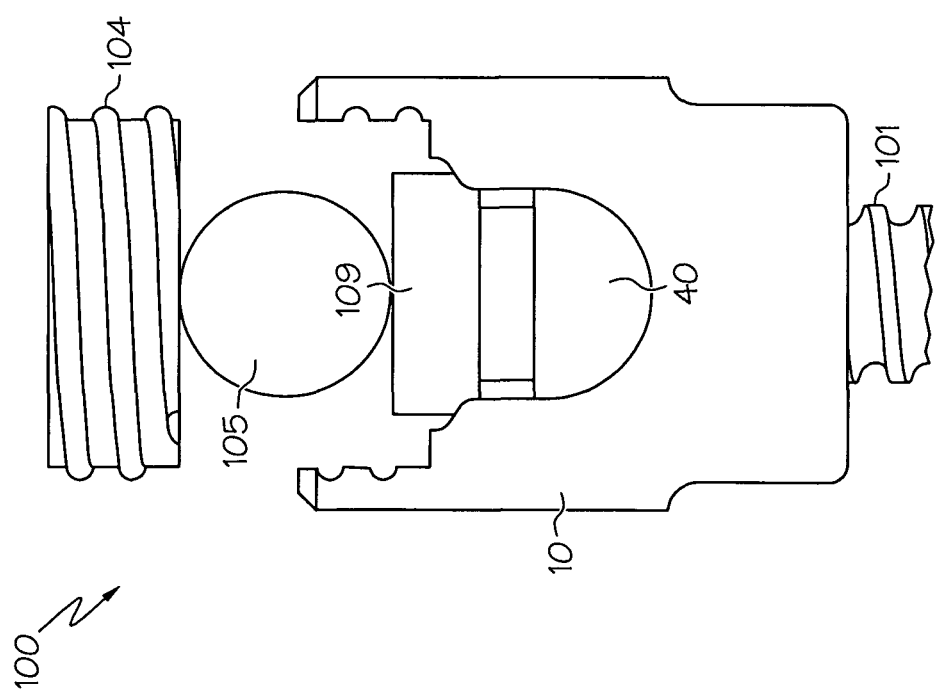
FIG. 10 is an exploded front view of a pedicle screw assembly, according to an embodiment of the present invention.

Referring now to FIGS. 10 and 11 there is illustrated an embodiment of a final modular pedicle screw assembly, with FIG. 10 showing a semi-exploded view and FIG. 11 showing a fully assembled view. Pedicle screw assembly 100 includes bone screw 101, rod holding element 10, insert (uniplanar 70 or monoaxial 40), rod 105, and set screw 104. In the final assembly of FIG. 11, rod 105 is firmly held in position.

Comparing FIG. 10 to FIG. 11 illustrates further aspects of the modular pedicle screw embodiment 100. For example, it is noted that at the point of assembly in FIG. 10, rod 105 has not yet come to a final position of rest. Screw head 109 projects through insert 40, 70, and rod holding element 10 is still free to move generally along the length of screw 101. Likewise, at this point of assembly inserts 40, 70 are free to move relative to rod holding element 10, as previously described. That is, a uniplanar insert 70 can move in its plane of freedom; however the monoaxial insert 40 would be restricted, because of the tab/notch fit, except to move generally upward, with respect to the orientation of FIG. 10. Rod 105 is also free to move relative to rod holding element 10. Thus, at this point of the assembly, a surgeon would typically bring the elements into alignment, as shown in FIG. 10; and then, using the freedom of movement permitted, the surgeon could make what adjustments to that alignment the surgeon desires. And once the elements are suitably aligned, the surgeon can begin to make the final assembly as follows.

A surgeon would begin to press downward, relative to the orientation of FIG. 10, for example on set screw 104. In a related fashion, the surgeon could pull upward (again relative to the orientation of FIG. 10) on rod holding element 10. As a result of these movements, screw head 109 passes into the receiving area 77 of insert 70, rod 105 passes into the saddle area 11, and set screw 109 approaches threading area 19 of rod holding element 10. It is noted that the profile dimension of screw head 109 is such that it can pass into receiving area 77 of insert 70 without significant resistance. As set screw 104 approaches threading area 19, set screw 104 may be rotated so that set screw threads 110 engage threading area 19. The further rotation of set screw 104 continues to move set screw 104 in a generally downward direction (relative to the orientation of FIG. 10), which movement brings bottom surface 14 of set screw 109 into further contact with rod 105. The movement of rod 105 likewise tends to move screw head 109 so that head 109 tends to move towards receiving area 77. In this manner the further rotation of set screw 109 continues to move the elements into an assembled configuration until the point of final assembly is reached as shown in FIG. 11.

It will also be appreciated by those skilled in the art that a modular pedicle screw assembly, preferably partially assembled, can also be secured in a pedicle bone prior to final assembly. For example, in one common practice, bone screw 101 can be assembled with rod holding element 10 and insert 40, 70. Bone screw 101 can then be inserted into the patient's pedicle bone. Once bone screw 101 is anchored to the patient's pedicle bone, the bottom of rod holding element 10 contacts the bone which exerts an upward pressure on the rod holding element 10. However, the pressure exerted upwardly by the bone against rod holding element 10 is not sufficient to prevent a uniplanar insert 70 from translating within rod holding element 10. The final locking of the assembly occurs when rod 105 is added to the assembly and is pressed downward by set screw 104. It is further to be appreciated in the general positioning and placement that surgeons are careful not to pull upwardly on these assemblies because in a degraded or diseased pedicle bone the screws can be uprooted with such an upward force.

Figure 21:
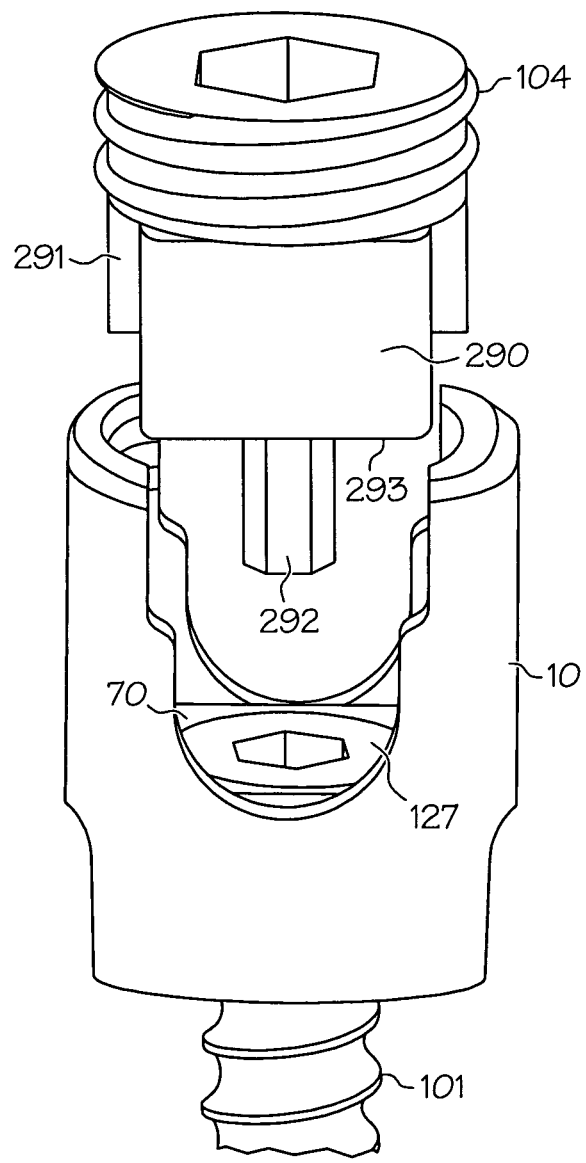
FIG. 21 is an exploded view of a pedicle screw subassembly using an assembly tool, according to an embodiment of the present invention.

In a further embodiment, the placement of a modular pedicle screw can be assisted with the use of an assembly tool. Referring now to FIG. 21 there is shown an exploded view of an exemplary embodiment of assembly tool 290 positioned with respect to rod holding element 10 and set screw 104. In a preferred embodiment, assembly tool 290 includes tabs 291 which can align and join with reciprocal groove structures (not shown in FIG. 21) on rod holding element 10 as previously described. Assembly tool 290 further includes bit 292, which as illustrated can be hex shaped (or otherwise shaped) in order to fit within the reciprocal space on bone screw 127. A surgeon or surgical assistant may place assembly tool 290 into rod holding element 10 by aligning pins 291 with grooves. Further, the hex bit 292 is aligned with the bone screw 101, and set screw 104 is then joined with rod holding element 10. Assembly tool 290 preferably has a flat surface or top (not shown) so that as set screw 104 is screwed into rod holding element 10, set screw 104 contacts the flat surface and thereby exerts a downward force on assembly tool 290. Additionally, assembly tool 290 preferably includes shoulder surface 293. In one embodiment, shoulder surface 293 is substantially planar so that as assembly tool 290 is pressed against insert 70 and bone screw head 127, shoulder 293 tends to force bone screw head 127 to recede within the receiving area of insert 70. A surgeon can use a hex tool (or other kind of tool) to tighten set screw 104. As set screw 104 is further tightened, it ultimately pushes assembly tool 290 into a bottomed out position. In this position, assembly tool 290 holds bone screw 101 into a final assembled position relative to insert 40, 70 and rod holding element 10. Taking advantage of the now positioned assembly tool 296, the surgeon can further apply torque to set screw 104 which thereby serves to rotate the entire assembly, including bone screw 101. In this manner bone screw 101 along with the entire assembly can be placed in a desired position relative to the patient's pedicle bone.

The assembly tool 290 illustrated in FIG. 21 provides advantages in the placement and formation of pedicle screw assemblies over other known methods. In a first instance, assembly tool 290 prevents bone screw 101 from moving out of axis with respect to rod holding element 10 when being inserted in the patient's bone. This phenomenon of movement, sometimes referred to as toggling, is an undesirable feature of other systems. Further, assembly tool 290 ensures that bone screw 101 remains in a desired alignment with the driver being used to insert the screw. The driver/tool is inserted into the set screw and thereby rotates the entire assembly. Thus the torsional force applied by the surgeon to the driver is advantageously aligned with bone screw 101 which allows the surgeon to confidently proceed with bone screw 101 placement.

In one embodiment it is desired that the configuration of screw head 109 closely matches the related configuration of receiving area 77 of insert 70 (as receiving area 47 of insert 40). In this manner once screw head 109 is fully assembled so as to drop fully into receiving area 77, the closely matching configuration restricts the movement of screw head 109 relative to insert 70. Thus, rod holding element 10, rod 105, and screw 101 are also held into a desired position.

Referring now to FIG. 11 it is noted that the various elements have come into a final position and are significantly secured in that position. Rod 105 rests in rod cradle/saddle area 11, and the saddle arms 20 that partially define saddle area 11 are in contact with rod 105. Preferably the width defined by saddle area 11 closely matches the diameter of rod 105 such that rod 105 is not unduly restricted in moving to a bottomed position within saddle area 11, and once in the bottomed position, as shown in FIG. 11, rod 105 is substantially restricted from side-to-side movement relative to the orientation of FIG. 11.

FIG. 11 also illustrates the point of interface 108 between rod 105 and upper surface 46 or 76 of insert 40 or 70. The point of interface 108 indicates that rod 105 comes to final rest against surface 46, 76 rather than the bottom point 18 of saddle area 11 in the illustrated embodiment. (In an alternative embodiment discussed further herein, rod 105 can rest in whole or part on bottom point 18 of saddle area 11). It is further noted that the force exerted by rod 105 against insert 40, 70 holds insert 40, 70 firmly against bearing surface 13 of rod holding element 10, and thus insert 40, 70 is positioned with respect to rod holding element 10.

Referring now to FIG. 20, there is shown a further illustration of rod holding element 10. FIG. 20 shows a bottom view of rod holding element 10, and in particular the figure illustrates screw hole opening 16. As previously explained, screw hole opening 16 is configured so as to allow shaft 128 of a pedicle screw to pass therethrough. FIG. 20 also illustrates the further preferred embodiment in which screw hole opening 16 is slightly oblong or elliptical in its shape, rather than substantially round, such that the dimension x 24 is greater than dimension y 26, each of which is substantially perpendicular to the other. This arrangement allows shaft 128 to have greater linear movement in the direction that aligns with dimension x 24.

The rod holding element with elliptical screw hole opening 16 may be advantageously used with uniplanar insert 70. It is noted that dimension x 24 is preferably aligned so as to present a particular configuration with uniplanar insert 70 that would be positioned within rod holding element 10. The plane of movement that uniplanar insert 70 would move in is a plane of movement that is also generally aligned with dimension x 24. Thus, when a bone screw passes through uniplanar insert 70, and shaft 128 of bone screw passes through screw hole opening 16, the planar movement of uniplanar insert 70 will not be unduly impeded as shaft 128 is also allowed some freedom of movement within the space of screw hole opening 16. As a further detail, it will be appreciated that dimension y 26 should be configured with a length at least as large as the diameter of bone screw shaft 128.

Finally, while the preferred embodiment of screw hole opening 16 has been illustrated in FIG. 20 as generally elliptical in shape, opening 16 could take other configurations, such as, for example a generally rectangular shape, or a generally rectangular shape with curved corners. It is also contemplated that the shape of opening 16 could follow a generally rectangular shape, however a rectangle with somewhat curved sides.

Figure 12A:
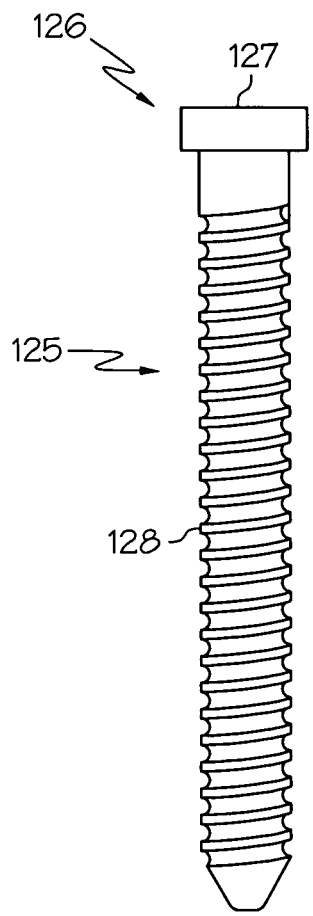
FIG. 12 is a perspective view of bone screw embodiments for use with embodiments of the present invention.
Figure 12B:
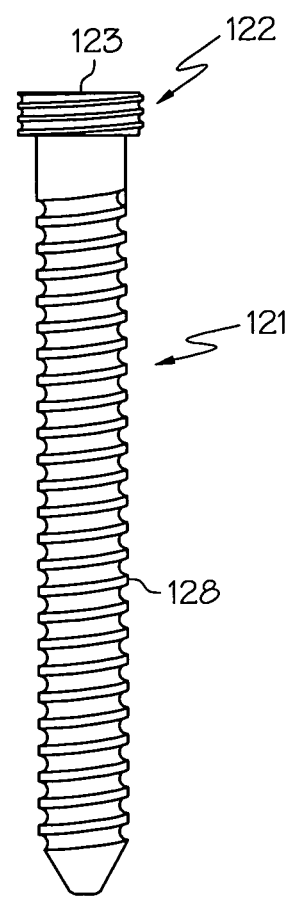

Referring now to FIG. 12 there are shown two varieties of screws, and at least these two screw varieties may be used with embodiments of the modular pedicle screw system. Screw 121 includes a head 122 that has threads 123, and screw 121 may thus also be referred to as a locking threaded screw. Screw 125 includes a head 126 with no threads, and screw 125 may be referred to as a non-locking screw or a flange-top screw. Screw 125 includes flange 127 positioned on its head 126. Flange 127 is preferably shaped to match the configuration and area defined by receiving area 47, 77 of insert 40, 70. The flange and receiving area could be tapered to form a press fit when assembled, held together by friction between mutual mating conical surfaces. The bone screws for use with the pedicle screw assembly also typically include a shaft 128, and shaft 128 may include shaft threads 130. All threads on both the bone screws and set screw are exemplary only and do not represent the actual thread pitch and taper.

Figure 14:
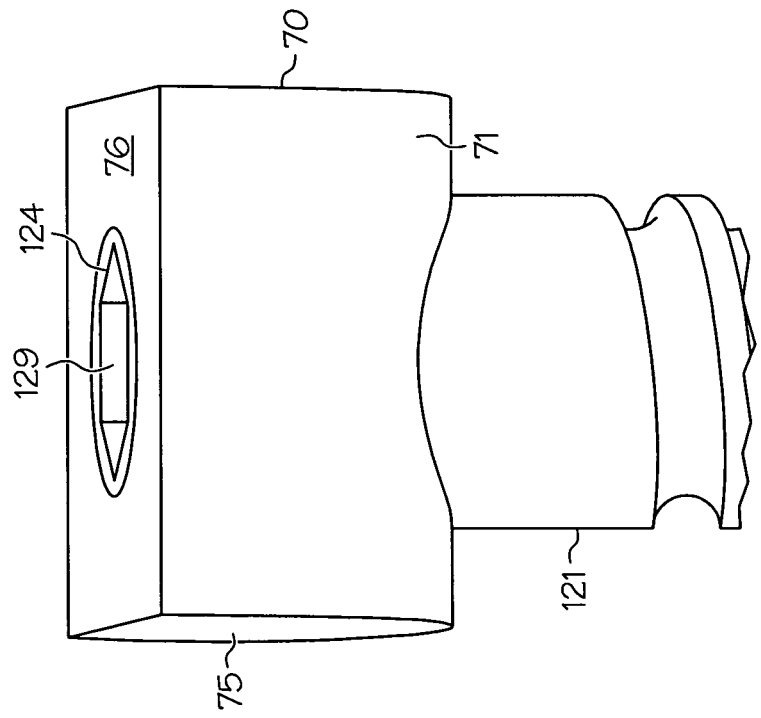
FIG. 14 is a perspective view of a threaded bone screw and uniplanar insert, according to an embodiment of the present invention.
Figure 13:
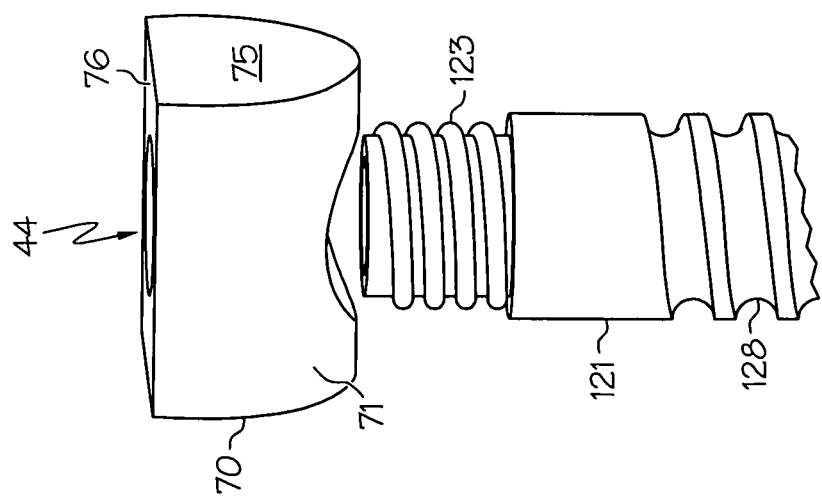
FIG. 13 is an exploded view of a threaded bone screw and threaded uniplanar insert, according to an embodiment of the present invention.

Referring now to FIGS. 13 and 14 there is illustrated an embodiment of a threaded screw 121 configured so as to be attached to a uniplanar insert 70. Thus in the embodiment of FIG. 13 uniplanar insert 70 includes a reciprocal threading 44 for bonding with the matching threads 123 of threaded screw 121. In the illustrated preferred embodiment, the threaded head 123 screws into a uniplanar or monoaxial insert on the underside of the insert, rather than a flanged head being inserted into the receiving area from above. Essentially, the insert 40, 70 when screwed together with the pedicle screw 121 acts as a modular screw head. The function remains unchanged from the monoaxial and uniplanar designs. Insert 70 can be joined to threaded screw 121 by rotating insert 70 and/or threaded screw 121 so as to engage the reciprocal threading 44 with threads 123. FIG. 13 illustrates threaded screw 121 and insert 70 in an exploded view. FIG. 14 illustrates threaded screw 121 joined with insert 70. FIG. 14 further illustrates how, in a preferred embodiment, the top 124 of threaded screw does not project beyond upper surface 76 of insert 70 to any significant extent, which allows a rod (not shown) to lay substantially flush against upper surface 70. Additionally, FIG. 14 illustrates how threaded screw 121 can include recessed area 129 for receiving a tool; and as known in the art, recessed area 129 may be configured as a socket with hexagonal walls (by way of example only) for receiving an Allen wrench. Although not illustrated, a nonthreaded screw may similarly include a recessed area.

Use of the threaded screw head embodiment can assist in locking the bone screw into the insert. The joinder achieved by the mutual threading of the bone screw and the insert can increase the rigidity of the screw/insert assembly and help to prevent movement of the screw relative to the insert. The locking threaded screw head can be useful in both the uniplanar and monoaxial configurations. It is also preferred that the locking threaded screw head embodiment be used with relatively larger diameter bone screws, i.e. those with a diameter greater than opening 26.

It is here noted that the screw of FIGS. 13 and 14 may be advantageously used in certain surgical procedures. For example, some surgeons prefer to affix a bone screw to a pedicle bone before any additional pedicle screw structure is attached to the bone screw. In such a technique the surgeon generally has a clearer view of the pedicle bone while placing the bone screw; additionally the technique allows the surgeon to shave bone material away from the area of the bone against which the rod holding element may ultimately be seated. Consistent with this technique, certain prior art systems, such as the Blackstone Icon system, are adapted so as to allow pedicle screw elements to snap onto the bone screw head after the bone screw has been placed in the pedicle bone. The above-noted embodiments of the pedicle screw system can also be assembled to the bone screw after the bone screw has been attached to the patient. For example, insert 70 can be placed in rod holding element 10. An assembly tool 290 and set screw 104, if desired, can hold these items in a desired relationship. Thereupon, this assembly can be screwed onto the threaded head 123 of bone screw 121.

Figure 15:
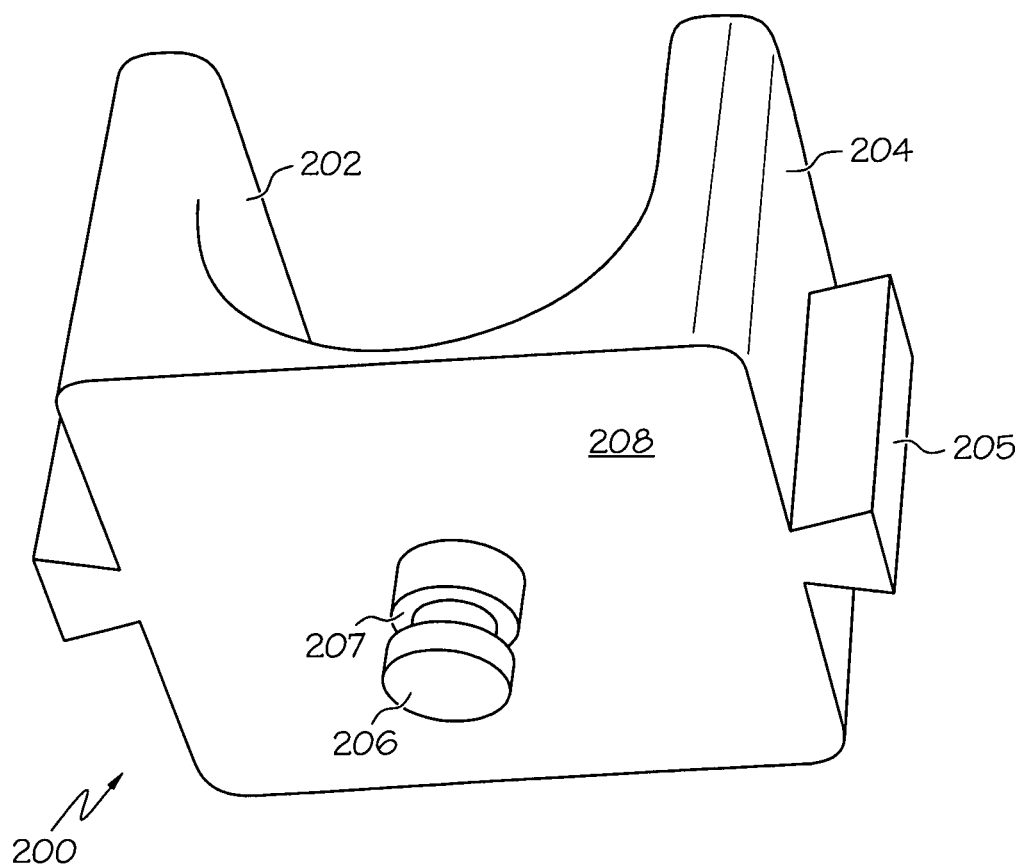
FIG. 15 is a perspective view of a rod adapter, according to an embodiment of the present invention.

Referring now to FIG. 15 there is illustrated an embodiment of rod adapter 200. As previously discussed, orthopedic therapies can call for rods having different qualities of strength and flexibility (among other criteria), and this is achieved in one respect by specifying rods with different diameters. To take two common examples in the industry, rods can be used that have a diameter of either 5.5 mm or 6.0 mm. The modular pedicle screw assembly can accommodate rods with different diameters, from as small as 3.0 mm up to and including 6.5 mm, by use of rod adapter 200.

Figure 17:
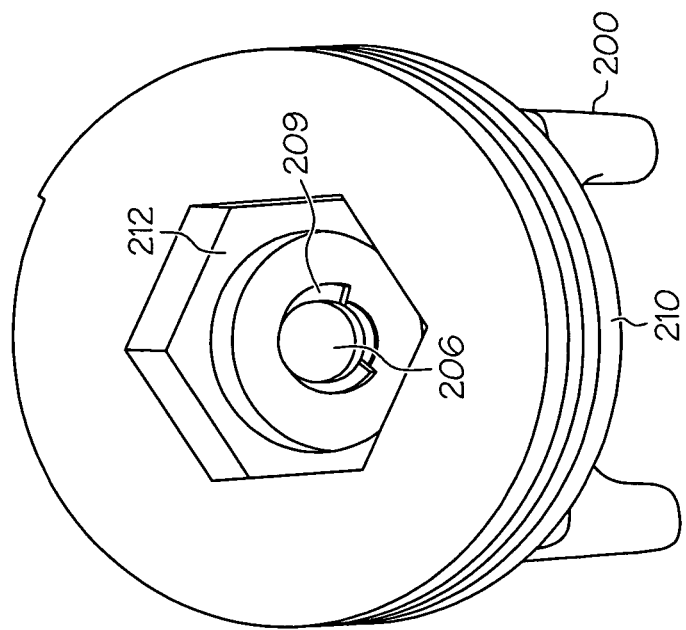
FIG. 17 is a top view of a rod adapter and set screw assembly, according to an embodiment of the present invention.
Figure 16:
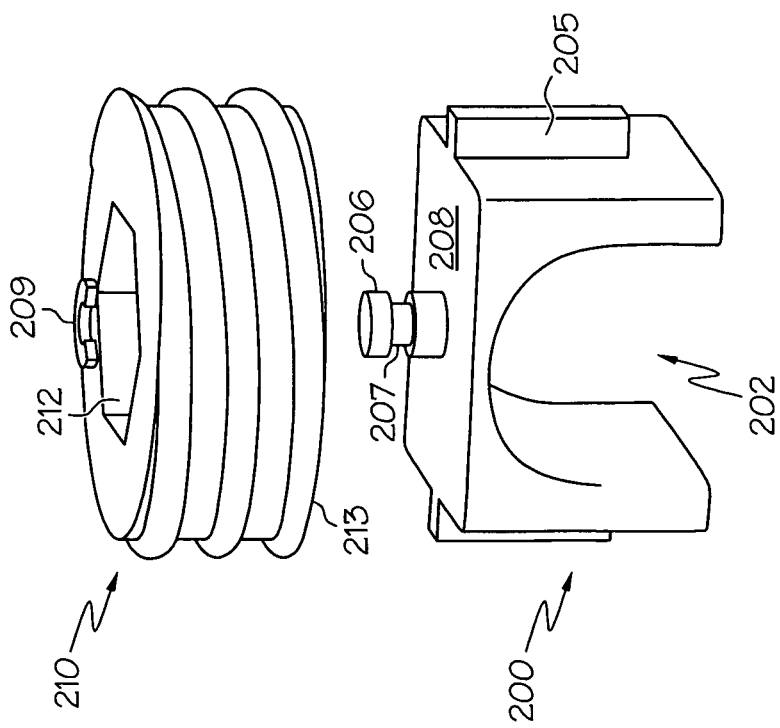
FIG. 16 is an exploded view of a rod adapter and set screw assembly, according to an embodiment of the present invention.

A preferred embodiment of rod adapter 200 generally includes a rod cradling portion 202, side wall 204, and rod adapter tab 205. In another embodiment, rod adapter 200 can further include a post 206 with an inset 207 for use with a locking ring device 209 as shown in FIGS. 16 and 17. Rod cradling portion 202 defines a generally semicircular surface with a radius adapted to substantially conform to the radius of the rod desired to be used. For example, in one embodiment, it is desired to use the rod adapter 200 to secure rods with a 5.5 mm diameter. In such a situation, rod cradling portion 202 would have a substantially similar diameter. Further, it is preferred that the surface of rod cradling portion 202 extend from a first end to the opposite end of rod adapter 200, as shown in FIG. 15, in order to provide a maximum surface area with which to secure a rod.

As with the monoaxial insert 40, the tab 205 on rod adapter 200 is configured to fit within the reciprocal space defined by notch 12 on rod holding element 10. FIG. 10 illustrates in particular that embodiment in which tab 205 assumes a dovetail configuration, and in such a situation, notch 12 would likewise have a reciprocal dovetail shape in order to receive tab 205. The function of this dovetail shape is to prevent the top portion of the rod holding element from spreading apart laterally when the set screw is tightened against the rod, thereby imparting a force between screw threads 19 and 104. Further, the improved alignment of threads 19 and 104 created by the tabs 205 prevent cross-threading and further mitigate the risk of rod holder head splay when the set screw is tightened. Walls 204 are generally planar structures configured to contact chamber walls 17 of rod holding element 10. In general, rod adapter 200 is configured to rest firmly within rod holding element 10.

Referring now to FIGS. 16 and 17, there is illustrated a subassembly of rod adapter 200 and set screw 210. In the illustrated preferred embodiment, set screw 210 includes a recessed area 212. Within recessed area 212 is an opening (not illustrated) which allows post 206 to pass therethrough. Recessed area 212 is generally configured so that when set screw 210 is fully positioned on rod adapter 200; i.e., when the bottom surface 213 of set screw 210 contacts upper surface 208 of rod adapter 200, post 206 of rod adapter 200 projects through set screw opening sufficiently such that inset 207 of post 206 is exposed within the recessed area 212. In this manner locking ring 209 can be disposed so as to lock with inset 207 and around post 206. This positioning of locking ring 209 with post 206 then acts to restrict the movement of set screw 210 away from rod adapter 200. However, locking ring 209 does not generally restrict the rotational movement of set screw 210 relative to rod adapter 200.

It is also noted that recessed area 212 can define, in whole or part, a configuration for receiving a torsional tool such as a screw driver or a hex wrench. In the embodiment illustrated in FIG. 12, for example, recessed area 212 defines walls within the body of the set screw 212 itself. The walls may define a hexagonal shape that can accommodate a hex wrench. A surgeon can thus dispose a tool within recessed area 212 in order to forcefully manipulate set screw 210. Optionally, a spacer (not shown), such as a washer structure, can be disposed between locking ring 209 and the set screw 210.

Figure 18:
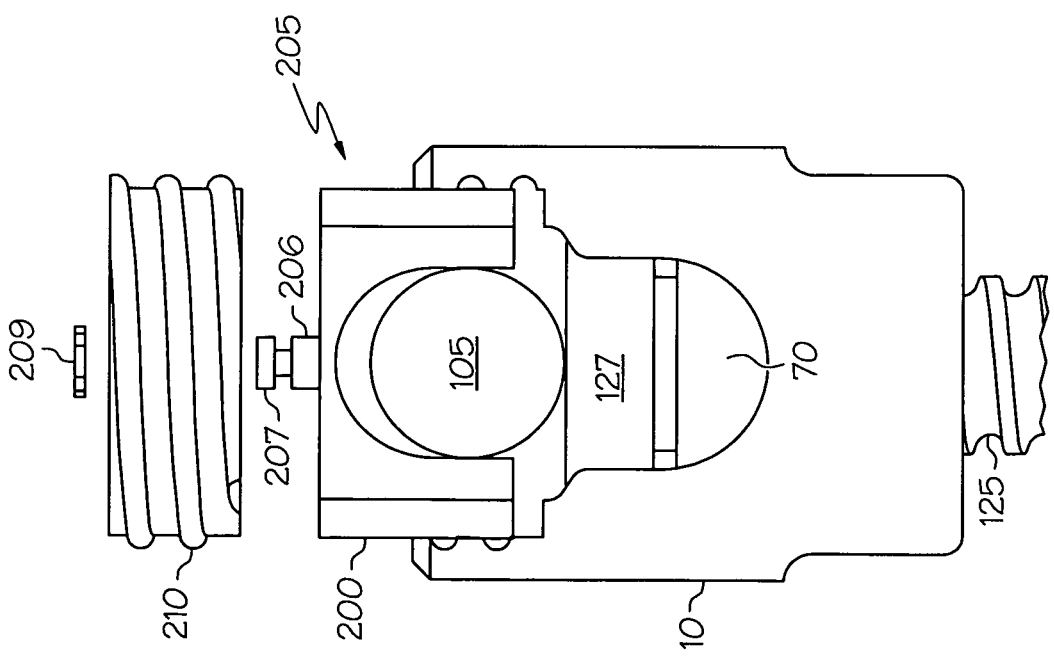
FIG. 18 is an exploded view of a rod adapter and pedicle screw assembly, according to an embodiment of the present invention.

The above subassembly of set screw 210 with rod adapter 200 is useful during surgical procedures in the following manner. Reference to FIG. 18 is useful in understanding the following description. Using elements earlier discussed, a surgeon has disposed a rod 105 within the chamber area 15 defined by rod holding element 10. Further, rod 105 may be resting against an upper surface 46 of an insert such as a monoaxial insert 40 or uniplanar insert 70. Portions of rod 105 may also rest against the saddle bottom 18 defined by rod holding element 10. However, if rod 105, such as a 5.5 mm rod, is somewhat undersized for the given rod holding element 10, rod 105 will experience some lateral movement within the rod holding element 10. It is generally desired to restrict this rod movement as the pedicle screw reaches its final assembly, and here is where the rod adapter subassembly comes into play. Rod adapter 200 can now be positioned so that rod cradling portion 202 surrounds the upper portion of rod 105. As the rod adapter 200 is so positioned, tabs 205 are aligned with notches 12. Then, as rod adapter 200 is moved in a generally vertical downward position so as to fully engage the rod 105, set screw 210 (previously assembled with rod adapter 200) comes into contact with threaded area 19 of rod holding element 10. Locking ring 209 does not allow set screw 210 to dislodge from rod adapter 200; however, it does permit set screw 210 to rotate. Thus, the surgeon can manipulate set screw 210 to rotate such that threads of set screw 210 engage with the reciprocal threaded area 19 of rod holding element 10. This manipulation may be a hand manipulation or a tool-assisted manipulation. Further, the surgeon can ultimately exert a desired amount of torque or tortional force on set screw 210 so that rod adapter 200 forcefully engages with rod 105 and thereby securely holds rod 105 in a desired position. Further, the degree of contact between the surfaces of rod 105 and the closely matching rod cradling portion 202 provide a sufficient level of contact so that rod 105 cannot easily move laterally relative to rod adapter 200.

The subassembly of rod adapter 200 to set screw 210 is additionally important to reduce the time needed during surgery. The use of such a subassembly, which can be constructed prior to surgery, eliminates the amount of time needed during surgery that would otherwise be required to put together these parts. Furthermore, it is generally desired to reduce the number of repetitive or fatiguing steps that must take place during surgery, and moving the subassembly to a time period outside the surgical theater achieves that advantage. This advantage particularly increases in importance where multiple such screw assemblies will be employed in the overall surgical procedure.

Figure 19:
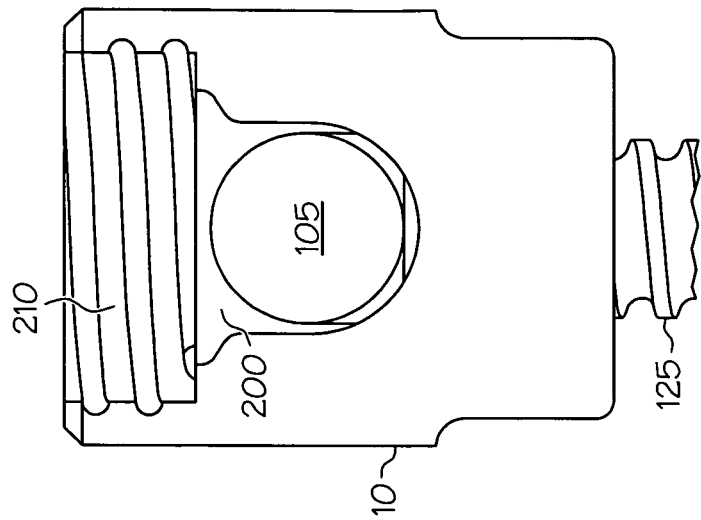
FIG. 19 is a front view of a rod adapter and pedicle screw assembly, according to an embodiment of the present invention.

Referring now to FIG. 19 there is shown a further embodiment of a fully configured pedicle screw assembly. FIG. 19 is also useful in illustrating one significant aspect of the function of rod adapter 200. As previously mentioned, rod adapter 200 is employed in those situations where the rod to be used during the surgical procedure is smaller than would normally fit in the saddle area 11 of rod holding element 10. Thus, FIG. 19 shows how the diameter of the saddle area 11 is indeed larger than the diameter of rod 105 disposed within saddle area 11. Were it not for rod adapter 200, rod 105 could more easily experience a side-to-side motion (relative to FIG. 19) within the saddle area 11 nor would the smaller diameter rod exert the necessary downward force onto the insert when the set screw is tightened. However, rod adapter 200, shown with a diameter that closely matches rod 105, a diameter that is less than saddle area 11 diameter, closely surrounds rod 105 and acts to prevent that movement. The rod adapter 200 also increases the surface area of contact with the superior aspect of rod 105 as compared to the flat bottom profile of the set screw alone. It should also be noted that a preferred embodiment would use a rod adapter 200 for all rod sizes, even those that fill the entire width of the saddle, to take advantage of the antisplay properties and increased area of contact discussed previously.

In a further embodiment, the modular pedicle screw system can be configured to allow for a dynamic stabilizing system. Referring again to FIG. 11 and FIG. 19 (the assembly with a rod adapter), it was noted that in the final assembly of one preferred embodiment, rod 105 rests against upper surface 46 or 76 of insert 40, 70 rather than resting against saddle area 11 of the rod holding element 110. In such a scenario, once rod 105 is inserted and the top set screw 104 is tightened, there will be no motion of the screw 104 relative to rod holding element 10 due to the compression created at the rod—insert interface 108. In the same manner as a traditional polyaxial screw, the rod compresses the bearing surface, insert, and screw head together to form a stable construct. However, with a simple modification of insert 40 and 70 (for example, by reducing the height dimension of insert slightly so that rod 105 does not compress insert 40, 70 but lies on the bottom point of saddle 11) the insert 70 will remain able to pivot within the rod holding element 10. In a preferred embodiment of such dynamic stabilization, in the final assembly rod 105 is also held at its upper position by the rod adapter. This can be useful in creating a dynamic system that allows for some motion between the vertebrae that are spanned by rod 105, which more typically creates a rigid system.

There can be disadvantages to a rigid system in some instances that can be ameliorated through a "dynamic stabilization." For example, the use of rods that have flexible sections has been attempted. However, weakness of the flexible rod structure, movement in multiple degrees of freedom, and repeated stresses may lead to failure of the system and other complications. The modular system described herein allows the rod holder to be dynamic, rather than the rod itself. From a biomechanical perspective, it is advantageous to dynamize the rod holding element because the degrees of freedom in the dynamic system can be limited by choosing the appropriate insert and the allowed motion can be aligned with the natural motion of the spinal segment being stabilized.

In a further embodiment, an insert may be eliminated altogether as a separate piece in the assembly. In this embodiment, the head of the bone screw is machined in the same shape, or substantially the same shape, as either the uniplanar insert 70 or monoaxial insert 40. Essentially two pieces are replaced with a single piece, which may further lead to time savings during surgery procedures and cost savings from machining fewer parts in total. Functionally the combined screw insert assembly is similar to the previously enumerated monoaxial and uniplanar designs but the machining process and parts are different.

Figure 22:
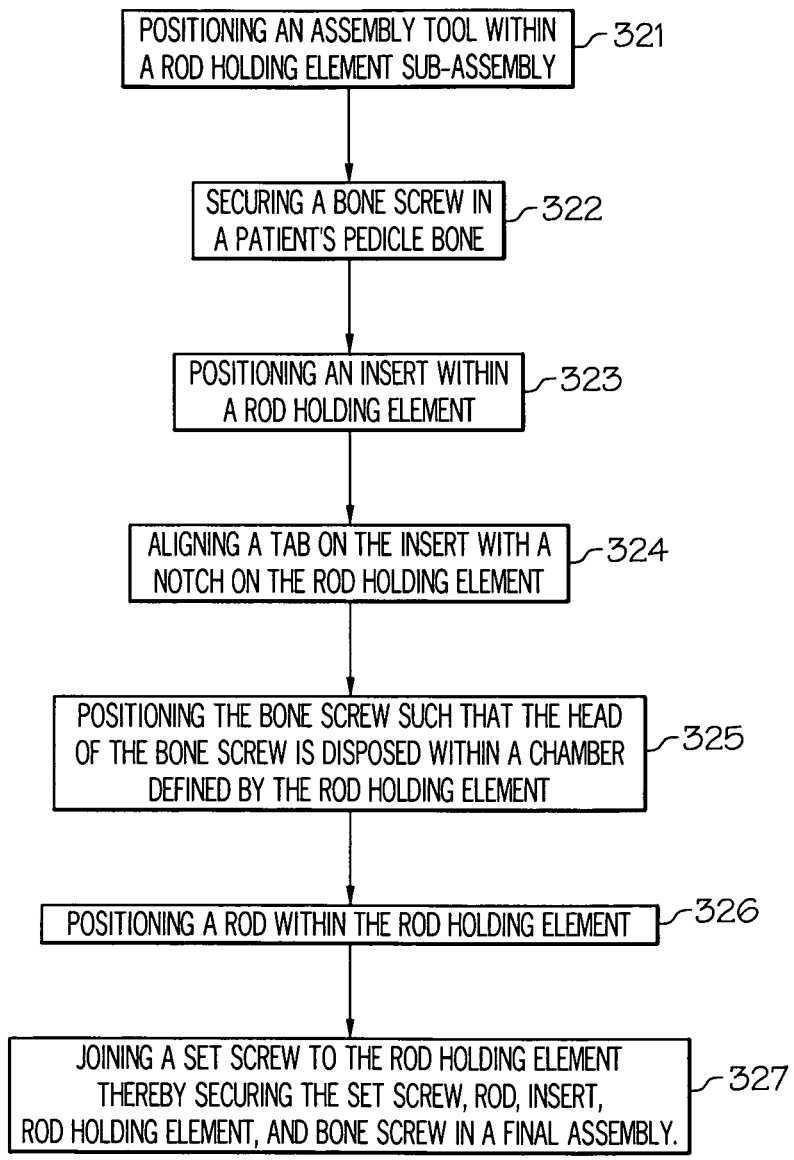
FIG. 22 is a flow chart showing process steps in a surgical procedure, according to an embodiment of the present invention.

As has been mentioned, embodiments of the modular pedicle screw system can be used with various surgical techniques and procedures as practiced in orthopedic surgery. Referring to FIG. 22, there are listed some exemplary steps that may be followed in one such method of usage. In step 321, a surgeon may begin the process by creating a subassembly comprising a bone screw, insert, assembly tool, rod holding element, and set screw. This advantageously secures the bone screw in a desired relationship relative to the rod holding element. Further, the bone screw can then be set in the patient's pedicle bone, step 322, by applying a hand tool to the set screw, which, because of the assembly tool's linkage with the bone screw, applies torsional force to the bone screw. It will be appreciated that in other embodiments, such as the embodiment described previously in which the bone screw includes top threading, the bone screw may be applied directly to the pedicle bone. Step 323 calls for positioning an insert within the rod holding element. This step may occur as part of the preassembly construction, step 321 or after the bone screw has been positioned, depending on the option selected. Step 324 which calls for aligning a tab on the insert with a notch on the rod holding element is an optional step in the overall step of placing the insert if the insert is equipped with such a structure. In step 325, the head of the bone screw is positioned such that the head of the bone screw is disposed within the rod holding element chamber. Again, depending on the surgical option, this may occur in constructing the preassembly of step 321. Optionally, this step may occur after the bone screw has been placed in the patient.

In step 326 a rod is placed within the rod holding element. It will here be appreciated that in those embodiments that use an assembly tool, the subassembly that includes the assembly tool must be disassembled (the set screw must be removed) and the assembly tool must be removed. Once the assembly tool has been removed, the rod may be placed within the rod holding element. Thus, placement of the rod within the overall assembly typically takes place after placement of the bone screw. Once the rod has been positioned, the final assembly can be secured; i.e., the set screw can be joined to the rod holding element. And, as previously described, tightening of the set screw pushes against the rod, which in turn pushes against the insert until a desired tension is obtained. Note, that if dynamic tensioning is desired, the rod may also contact the lower saddle portion of the rod holding element.

Polyaxial Embodiments

Figure 23:
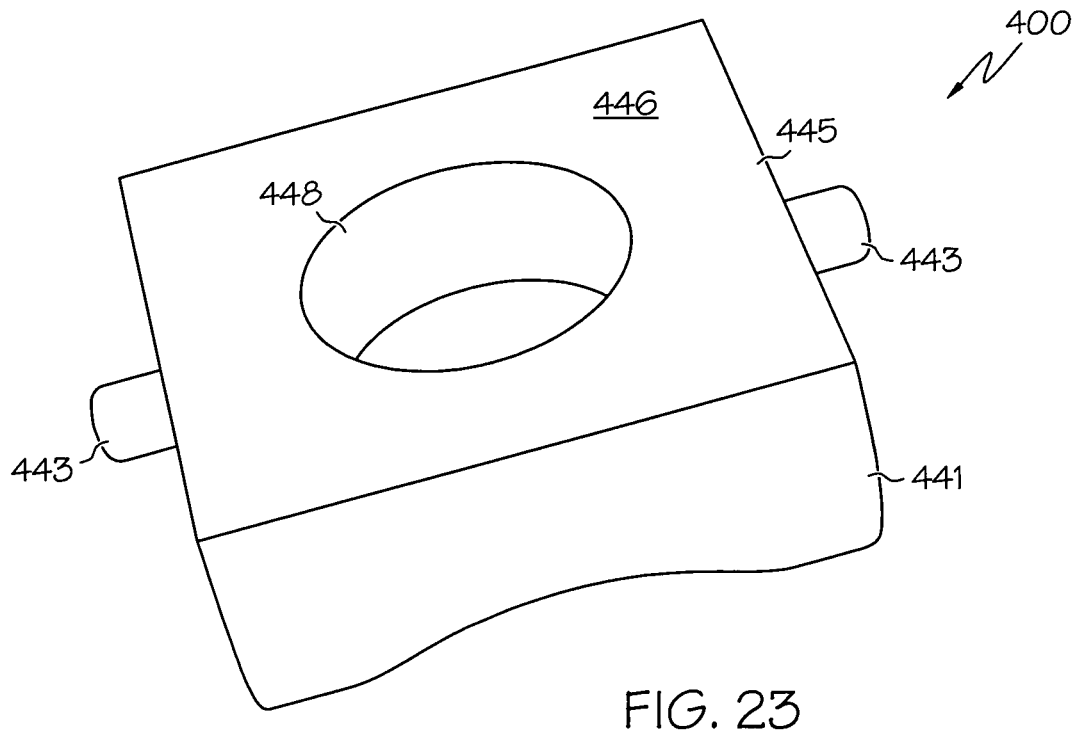
FIG. 23 is a perspective view of a polyaxial insert, according to an embodiment of the present invention.
Figure 24:
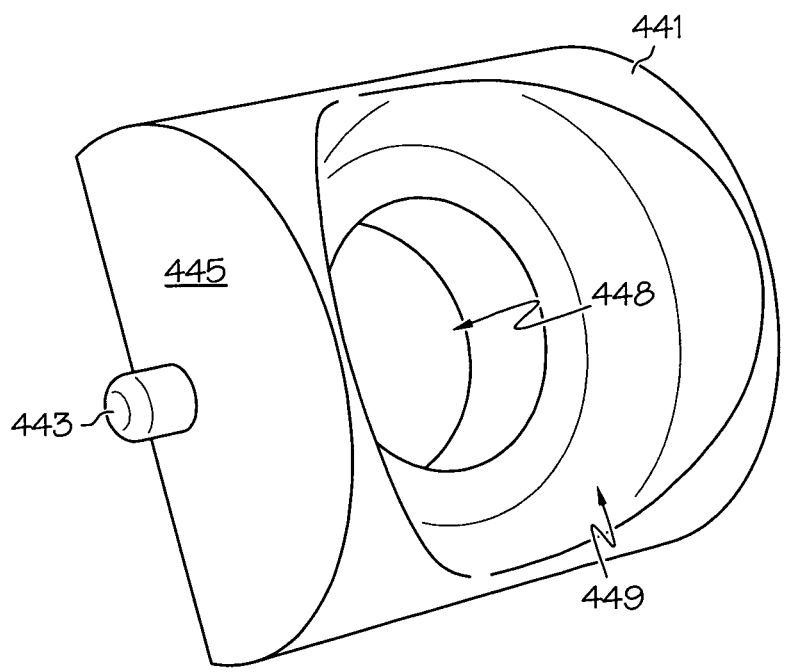
FIG. 24 is a bottom perspective view of a polyaxial insert, according to an embodiment of the present invention.

Referring now to FIGS. 23 and 24 there is shown an embodiment of a polyaxial insert 400. Polyaxial insert 400 is also configured to fit within chamber 15 of rod holding element 10. Polyaxial insert 400 thus includes bearing surface 441, side walls 445, upper surface 446, and screw hole 448. Polyaxial insert 400 further includes screw head bearing surface 449, as shown in FIG. 24. In a preferred embodiment, polyaxial insert 400 also includes guide pins 443 positioned to project from side walls 445.

The overall shape and configuration of polyaxial insert 400 allows it to fit within rod holding element 10. Side walls 445 preferably align closely with chamber walls 17 so as to restrict lateral movement of polyaxial insert 400. Polyaxial bearing surface 441 is preferably shaped with a curvature that substantially matches bearing surface 13 of rod holding element 10; and thus when polyaxial insert 400 is fully positioned within rod holding element 10 bearing surface 441 of polyaxial insert 400 makes substantial contact with bearing surface 13 of rod holding element 10. In the illustrated embodiment the matching of these bearing surfaces, the polyaxial bearing surface 441 and the rod holding element bearing surface 13, allows polyaxial insert 400 to rotate within chamber, on a plane of freedom, in a manner similar to uniplanar insert 70. In a preferred embodiment both the polyaxial bearing surface 441 and the rod holding element bearing surface 13 define a substantially circular curvature; however other curvatures are acceptable.

The preferred embodiment of polyaxial insert 400 illustrated in FIGS. 23 and 24 shows the insert having guide pins 443. However, polyaxial insert 400 can be configured without guide pins 443. Guide pins 443 are preferably configured as rounded, substantially circular, cylindrical projections. Guide pins 443 preferably have a diameter that allows them to pass through notch 12 of rod holding element 10; however, guide pins 443 do not project so far from side walls 445 so as to limit the movement of polyaxial insert 400 within chamber 15. Guide pins 443 are advantageously positioned when they are located on side walls 445 at a point that substantially corresponds to the center point of the geometric circle that is defined by bearing surface 441. Having that center point location, and given their rounded, cylindrical profile, guide pins 443 can rotate within notch 12 as insert 400 rotates. Further, by having such freedom to rotate, guide pins 443 do not restrict the rotational motion of polyaxial insert 400. Thus guide pins 443 facilitate the positioning and firm placement of polyaxial insert 400 while not restricting the insert's intended freedom of movement.

Alternatively, polyaxial insert 400 can be configured with tabs (not shown) that are substantially similar to locking tabs 43 positioned on monoaxial insert 40. And, as with the monoaxial insert 40, a polyaxial insert 400 that includes locking tabs 43 would have its freedom of movement restricted by the tabs 43.

It is additionally noted that guide pins 443 such as those illustrated in FIGS. 23 and 24 can also be placed on the uniplanar insert 70. Further, the embodiment of uniplanar insert 70 having generally cylindrical guide pins 443 would also have the advantages described above with respect to polyaxial insert 400.

Figure 25B:
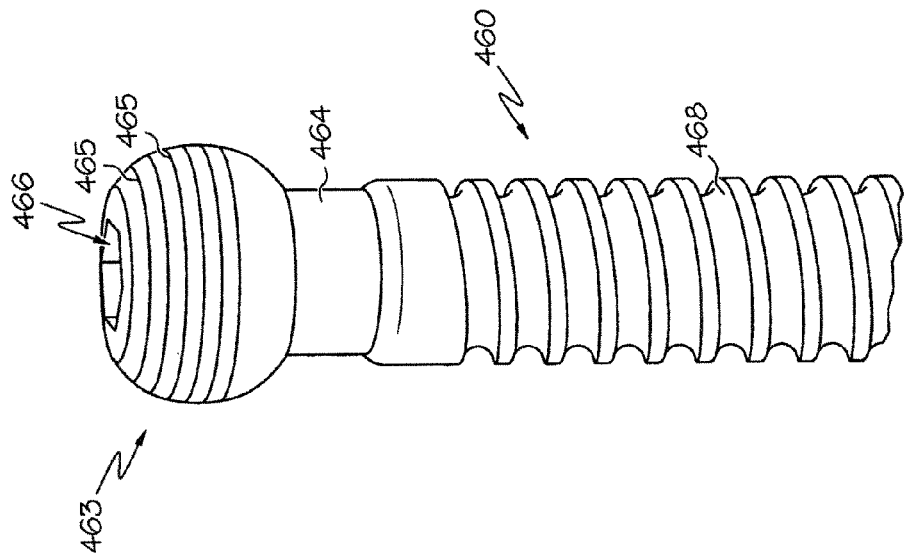
FIG. 25B is a front view of the polyaxial screw of FIG. 25A.
Figure 25A:
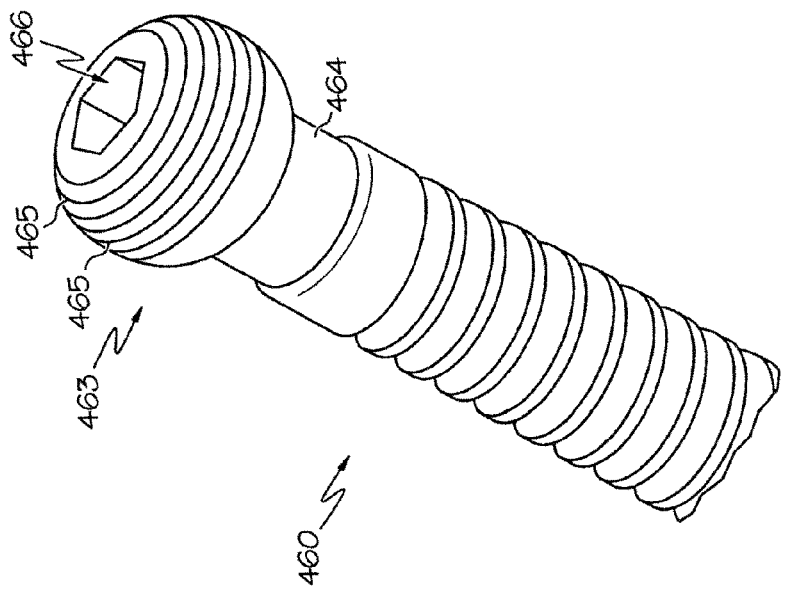
FIG. 25A is a perspective view of an exemplary embodiment of a polyaxial screw that may be used in conjunction with embodiments of the present invention.

Referring again to FIG. 24 it has been noted that polyaxial insert 400 includes screw head surface 449. This surface 449 is configured so as to receive a polyaxial screw head, transfer support to and from the screw, and ultimately lock the pedicle screw assembly into a desired position relative to the bone screw. Preferably surface 449 defines a partial hemisphere or other curvature that matches the geometry of a polyaxial screw head. One exemplary embodiment of the partially spherical head on a pedicle screw is shown in FIG. 25.

Referring again to FIG. 25 there is illustrated an embodiment of a polyaxial screw 460 that may be advantageously used in pedicle screw assemblies. Polyaxial screw 460 includes shaft 468, neck 464, and head 463. Shaft 468 may include any of the known threading structures, and shaft 468 is generally configured as known in the art to function as a pedicle screw. Head 463 is characterized by radial ridges 465. Head 463 may additionally have a recess or recessed area 466 which, as shown in the preferred embodiment, may itself be configured so as to receive a torsional tool. In the illustrated embodiment, recessed area 466 has a female hex shape so as to receive an Allen wrench.

In an alternative embodiment, rather than having radial ridges 465, head 463 may include other structures (not shown) such as bumps, grooves, non-radial ridges, or other surface anomalies which serve to increase the frictional lock between head 463 and surface 449 once a final assembly is created. As an additional alternative, surface 449 may also be configured with surface structures such as ridges, bumps, and the like so as to create the desired frictional lock. Further, ridges 465 or other friction-inducing structures may be positioned on both the upper surfaces and lower surfaces or even side surfaces of head 463. In this manner, screw head 463 can achieve frictional fixation or contact where it contacts structures both above and below the head 463 in the pedicle screw assembly.

Polyaxial screw 460 preferably includes neck 464 which can be a neck with a generally reduced diameter. The preferred reduced diameter neck 464 allows shaft 468 and thus screw 460 to move more freely within screw hole 16. The reduced diameter neck 464 includes any size neck diameter which allows head 463 to pivot against surface 449. In a further preferred embodiment, reduced neck 464 and hole 16 operate together so as to allow head to pivot with approximately a 60° range of motion. In such an embodiment, screw 460 can pivot up to approximately 30° from the vertical position. In other embodiments, screw 460 can pivot up to approximately 60° from the vertical position. The maximum range of motion is a factor of screw diameter and aperture size 26 with larger screws tending to have a more limited range of motion.

In a preferred embodiment, screw 460 and rod holding element 10 are mutually configured so that when screw head 463 is assembled so as to rest within chamber 15, but prior to final tightening, screw head 463 still has a freedom of motion. The freedom of motion allows the surgeon to position screw 460; then, upon final tightening of the modular assembly, screw 460 remains in the desired position. Referring again to FIG. 3 it is noted that rod holding element 10 includes a cut away area 27. Preferably this cut away area 27 defines an area in which screw head 463 is allowed to rotate and move. Cut away area 27 can comprise mutually opposing sections in rod holding element 10. Where screw head 463 defines a partial sphere, cut away area 27 can likewise be partially spherical in shape.

Still referring to FIG. 3, and also to FIG. 2, it is again noted that rod holding element 10 defines screw hole 16. Further, screw hole 16 is defined at its outer perimeter by head seating surface 14. Preferably hole 16 and head seating surface 14 are selected of a size such that screw shaft 468 can pass through; however, screw head 463 cannot pass completely out of chamber area 15 by passing completely past head seating surface 14. However, as further explained with respect to FIGS. 26 and 27, head 463 can partially, but not fully, extend past head seating surface 14. Thus, in one embodiment, head seating surface 14 acts as a restrictor to the movement of screw head 463. It is also noted that head seating surface 14 can exhibit different types of surfaces that mate with screw head 463. For example, the surface 14 may have a generally sharp edge, or a flat surface, or a generally rounded edge.

Figure 27:
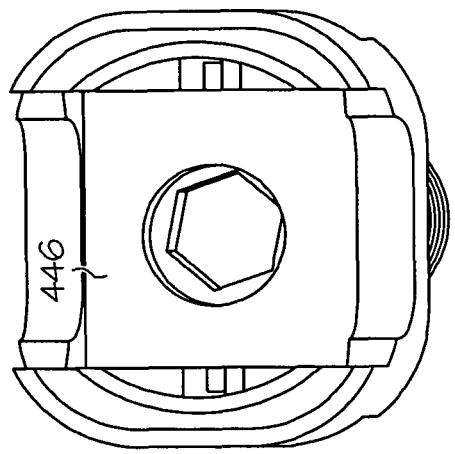
FIG. 27 is a top view of a partial polyaxial pedicle screw assembly, according to an embodiment of the present invention.
Figure 26:
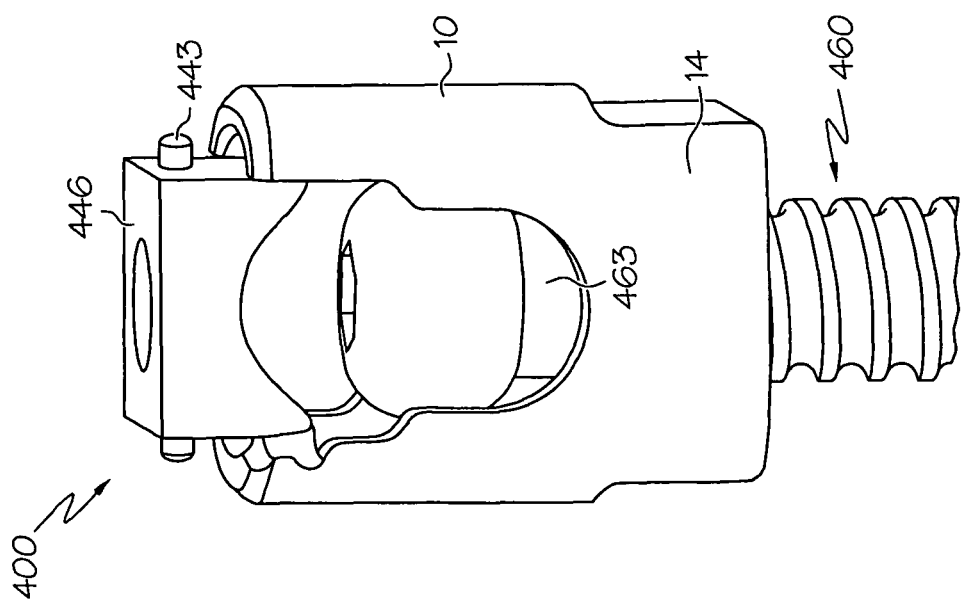
FIG. 26 is a partially exploded view of a polyaxial pedicle screw assembly, according to an embodiment of the present invention.

Referring now to FIGS. 26 and 27 the joining of a polyaxial modular pedicle screw assembly is described. Polyaxial screw 460 is positioned so that shaft 468 passes through screw hole 16 of rod holding element 10. Polyaxial screw 460 may be positioned such that a bottom portion of head 463 contacts head seating surface 14 of rod holding element 10. Polyaxial insert 400 is then positioned within chamber area 15 of rod holding element 10. When polyaxial insert 400 is initially positioned bearing surface 441 may contact an upper portion of screw head 463. Further, if polyaxial insert 400 includes guide pins 443, the guide pins 443 may be positioned within notch 12. Rod 105 (not shown in FIG. 26 or 27) can next be positioned within rod holding element 10 such that rod 105 contacts upper surface 446 of insert 400. Finally, set screw 104 can also be positioned so as to engage threaded area 19 of rod holding element 10.

It will be appreciated that in creating a polyaxial screw assembly, it is preferred to first assemble the elements into a preassembly configuration, adjust the elements, and then create a final assembly. The preassembly configuration holds the elements in their generally desired arrangement; however the elements are still free to move relative to one another and have not yet been locked into a final position. For example, in the preassembly configuration, set screw 104 has only been partially tightened so that the elements can not disassemble. Polyaxial screw 460 can be adjusted as can polyaxial insert 400, with respect to rod holding element 10 and rod 105. Thus in the preassembled configuration a surgeon can move and adjust the elements in the polyaxial assembly until a desired configuration is achieved. At that point, the surgeon can further tighten set screw 104 until the final assembled configuration is achieved. It will further be appreciated that set screw 104 can be gradually tightened so that the mobility of the elements becomes gradually lessened. Further, set screw 104 can be "backed off" or partially unscrewed so as to lessen the tightness of the assembly, and once the assembly has been loosened the elements therein can again be adjusted. In this manner, a surgeon can manipulate the polyaxial assembly until a desired configuration is achieved.

It is here recalled that a rod adapter 200 could be used with a uniplanar insert 70 or a monoaxial insert 40 as a means to use different sized rods with the rod holding element 10. Such a rod adapter 200 can also be used with a polyaxial insert 400. Again, rod adapter 200 allows different sized rods to be used in creating polyaxial assemblies while keeping the same rod holding element 10. Thus, the previous discussion regarding rod adapter 200 and its use in various assemblies is incorporated herein with respect to the polyaxial assembly. It is further noted that the steps shown in FIG. 22, steps for the assembly of a pedicle screw, can also be applied to embodiments of the polyaxial pedicle screw. Accordingly the discussion relating to FIG. 22 is also incorporated with respect to polyaxial pedicle screw embodiments.

The following discussion points refer generally to all pedicle screw embodiments unless specifically noted. Referring again to FIG. 1, it is to be noted that in the preferred embodiment, rod holding element 10 includes flats 21 on an outer surface of rod holding element 10. Flats 21 are typically a generally flat area, on mutually opposing sides of rod holding element 10, configured for receiving any number of surgical tools. By way of example, a wrench could be applied to the flats 21 to rotate the rod holding element directly. Similarly, as would be familiar to those skilled in the art of spinal fixation devices, a rod reducing tool could be placed on the flats as a secure anchoring point for a tool to forcefully guide the rod into the rod cradle when alignment by hand is difficult. Such a manipulation of rod holding element 10 may be useful at various stages of surgery rather than manipulating some other element of the system.

As previously mentioned, a dovetail configuration of mutually assembled elements can be useful in assembling and locking pieces into a desired arrangement. Thus, rod holding element 10 can be configured with a dovetailed notch 12 and rod adapter 200 can be configured with a dovetailed tab 205 where both tab 205 and notch 12 are mutually configured to match each other. Additionally, the monoaxial insert 40 can be configured with a dovetailed locking tab 43 that also reciprocally matches the dovetailed configuration of notch 12. This arrangement of elements is useful not only for firmly engaging pieces in a desired configuration; it can also help to prevent the head of the rod holder 10 from tending to splay outward when, as the set screw 210 is tightened, it exerts a force on the elements that tend to push outwardly against chamber walls 17 of rod holding element. The illustrated configuration of tabs and notches, where rod holding element notch 12 has a closed rather than open configuration, helps to resist that outward force. It is thus to be noted that the dovetail configuration described above with respect to the rod adapter 200 can be applied to other elements in the various pedicle screw embodiments, and is not limited to that single application.

Attachment means other than the described set screw 210 may also be used with the various pedicle screw embodiments described herein. For example an external nut can be applied as the fastening and tightening mechanism. Similarly, helically cut threads, which reduce cross-threading and head splay, may also be employed as a fastening and tightening mechanism.

It will be appreciated by those skilled in the art that a variety of thread patterns are known for use with pedicle screws. Thus, where a certain kind of thread pattern has been illustrated with a particular element, such as the threads by which the set screw is joined to the rod holding element or the thread pattern by which the pedicle screw itself is lodged in the bone, the illustrated thread pattern is presented for illustrative purposes only. The embodiments of the modular pedicle screw system can be used with a variety of different screw patterns and designs.

Additionally, bone screws may also vary beyond their thread pattern, and the embodiments described herein are generally useful with other varieties of bone screw than the particular examples described. More specifically, certain bone screws may have a cannulated design to assist in surgical placement and navigation to the correct location and angulation. Such cannulated bone screws may also be used with the described embodiments of the invention.

The materials that may comprise the various elements of the modular pedicle screw assembly are now discussed. Generally, any suitable material used for orthopedic implants may be employed. Particularly, those materials known to a practitioner skilled in the art that have been used for prior art pedicle screw designs may also be used in constructing the elements of the invention embodiments described herein. The rod holding element, the rod adapter element, and the insert element may likewise be fabricated of these same materials. Thus, by way of illustrative example only, titanium and stainless steel alloys may be used in fabrication.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out this invention, but that the invention will include all embodiments falling within the scope of the appended claims.

What is claimed is:

1. A polyaxial pedicle screw assembly comprising:
 a polyaxial pedicle screw having a shaft and head;
 a rod holding element that defines a screw hole opening, a curved bearing surface, a chamber, a saddle area, a cutaway area, a head seating surface, and a threading area;
 a polyaxial insert disposed within the chamber, wherein the polyaxial insert defines a curved lower insert bearing surface, a screw head bearing surface defined in and extending upwardly from the curved lower insert bearing surface, and an upper surface, wherein the curved lower insert bearing surface has a curvature that is substantially the same as the curvature of the rod holding element curved bearing surface;
 wherein the polyaxial insert is positioned within the chamber of the rod holding element such that the curved lower insert bearing surface of the polyaxial insert contacts the rod holding element curved bearing surface, and wherein the curved contact between the polyaxial insert and the rod holding element allows for pivoting motion of the polyaxial insert within the rod holding element;
 wherein the polyaxial pedicle screw is disposed so that a threaded portion of the shaft passes through the screw hole opening, and the polyaxial pedicle screw head contacts the screw head bearing surface of the polyaxial insert;
 a rod disposed to rest on the upper surface of the polyaxial insert; and
 a set screw joined to the threading area of the rod holding element so as to secure the rod to the upper surface of the insert and to lock the polyaxial pedicle screw and rod holding element into a desired position.

2. The assembly according to claim 1 wherein the rod holding element further defines opposing notches and wherein the polyaxial insert further comprises opposing guide pins positioned such that the each guide pin fits within the a respective notch when the polyaxial insert is disposed in the chamber.

3. The assembly according to claim 2, wherein polyaxial insert is configured to pivot within the rod holding element about an axis defined by the guide pins.

4. The assembly according to claim 2 wherein the guide pins are-substantially cylindrical in shape.

5. The assembly according to claim 4 wherein the guide pins are substantially cylindrical in shape whereby the polyaxial insert has freedom of movement in a plane.

6. The assembly according to claim 1 wherein the rod holding element further comprises a head seating surface disposed proximate to the screw hole, and wherein the polyaxial pedicle screw head contacts the head seating surface.

7. The assembly according to claim 1 wherein the polyaxial pedicle screw head further comprises surface structures.

8. The assembly according to claim 7 wherein the surface structures comprises ridges.

9. The assembly according to claim 1 further comprising a rod adapter connected to the set screw and wherein the rod adapter is disposed to engage with the rod.

10. The assembly according to claim 9, wherein the rod holding element further defines opposing notches having a dovetail configuration, wherein the rod adapter has opposing tabs having a reciprocal dovetail configuration, wherein each notch is configured to receive a respective tab.

11. A medical kit comprising:
a polyaxial pedicle screw having a shaft and head;
a rod holding element that defines a screw hole, a curved bearing surface, a chamber, a saddle area, a cutaway area, a head seating surface, and a threading area;
a polyaxial insert that defines a curved lower insert bearing surface, a screw head bearing surface defined in and extending upwardly from the curved lower insert bearing surface, and an upper surface, wherein the curved lower insert bearing surface has a curvature that is substantially the same as the curvature of the rod holding element curved bearing surface;
a set screw; and
a rod adapter,
wherein the polyaxial pedicle screw is configured to be disposed within the rod holding element so that a threaded portion of the shaft passes through the screw hole of the rod holding element, and wherein the rod holding element further defines opposing notches having a dovetail configuration, wherein the rod adapter has opposing tabs having a reciprocal dovetail configuration, wherein each notch is configured to receive a respective tab.

12. The medical kit according to claim 11 further comprising a rod.

13. The medical kit according to claim 11 further comprising a uniplanar insert and a monoaxial insert.

14. The medical kit according to claim 11 further comprising at least two rods having different diameters.

15. A method of forming a polyaxial pedicle screw assembly comprising the steps of:
providing a polyaxial pedicle screw having a shaft and head;
providing a rod holding element having a screw hole and a curved bearing surface;
providing a polyaxial insert defining a curved lower insert bearing surface and a screw head bearing surface defined in and extending upwardly from the curved lower insert bearing surface;
positioning the polyaxial pedicle screw relative to the rod holding element such that a threaded portion of the shaft of the polyaxial pedicle screw passes through the screw hole of the rod holding element;
positioning the polyaxial insert such that the screw head bearing surface of the polyaxial insert contacts the head of the polyaxial pedicle screw, and such that the curved lower insert bearing surface of the polyaxial insert contacts the rod holding element curved bearing surface;
positioning a rod within the rod holding element; and
joining a set screw to the rod holding element.

16. The method according to claim 15 wherein the step of positioning a polyaxial insert further comprises positioning the polyaxial insert such that guide pins of the polyaxial insert fit within notches of the rod holding element.

17. The method according to claim 16 further comprising the step of rotating the insert relative to the rod holding element by rotating the polyaxial insert about an axis defined by the guide pins.

18. The method according to claim 15 further comprising adjusting the position of the polyaxial pedicle screw relative to the rod holding element by moving the screw head at the screw head bearing surface of the polyaxial insert.

19. The method according to claim 15 further comprising positioning a rod adapter around the rod.

20. The method according to claim 15 further comprising fixing the polyaxial pedicle screw, the polyaxial insert, and the rod holding element into a desired substantially immovable configuration.

* * * * *